US009719987B2

(12) United States Patent
Mañez Mendiluce

(10) Patent No.: US 9,719,987 B2
(45) Date of Patent: Aug. 1, 2017

(54) IMMUNOADSORBENT COMPOSITIONS COMPRISING HYALURONIC ACID OLIGOSACCHARIDES

(71) Applicant: FUNDACIO INSTITUT D'INVESTIGACIO BIOMEDICA DE BELLVITGE (IDIBELL), L'Hospitalet de Llobregat (ES)

(72) Inventor: Rafael Mañez Mendiluce, L'Hospitalet de Llobregat (ES)

(73) Assignee: FUNDACIO INSTITUT D'INVESTIGACIO BIOMEDICA DE BELLVITGE (IDIBELL), L'Hospitalet de Llobregat (ES)

( * ) Notice: Subject to any disclaimer, the term of this patent is extended or adjusted under 35 U.S.C. 154(b) by 0 days.

(21) Appl. No.: 14/421,555

(22) PCT Filed: Aug. 12, 2013

(86) PCT No.: PCT/EP2013/066825
§ 371 (c)(1),
(2) Date: Feb. 13, 2015

(87) PCT Pub. No.: WO2014/026950
PCT Pub. Date: Feb. 20, 2014

(65) Prior Publication Data
US 2015/0192576 A1   Jul. 9, 2015

(30) Foreign Application Priority Data
Aug. 13, 2012  (EP) .................... 12382325

(51) Int. Cl.
| | | |
|---|---|---|
| A61K 31/702 | (2006.01) | |
| G01N 33/53 | (2006.01) | |
| G01N 33/548 | (2006.01) | |
| G01N 33/564 | (2006.01) | |
| A61K 35/16 | (2015.01) | |
| A61K 35/18 | (2015.01) | |

(52) U.S. Cl.
CPC ....... *G01N 33/5308* (2013.01); *A61K 31/702* (2013.01); *A61K 35/16* (2013.01); *A61K 35/18* (2013.01); *G01N 33/548* (2013.01); *G01N 33/564* (2013.01); *G01N 2800/52* (2013.01)

(58) Field of Classification Search
None
See application file for complete search history.

(56) References Cited

U.S. PATENT DOCUMENTS

| | | | | |
|---|---|---|---|---|
| 5,352,670 A | * | 10/1994 | Venot | A61K 31/70 435/175 |
| 5,651,968 A | | 7/1997 | Good | |
| 5,759,993 A | * | 6/1998 | Venot | A61K 31/70 514/20.9 |
| 7,049,124 B1 | * | 5/2006 | Kordowicz | C12N 9/2408 424/94.5 |
| 7,511,026 B2 | * | 3/2009 | Kato | A61K 31/70 514/23 |
| 2008/0182983 A1 | * | 7/2008 | Asari | A61K 31/702 536/123.1 |
| 2012/0225814 A1 | * | 9/2012 | Hanjaya-Putra | A61L 27/52 514/7.6 |

FOREIGN PATENT DOCUMENTS

| | | |
|---|---|---|
| WO | 0210755 | 2/2002 |
| WO | 2009140897 | 11/2009 |
| WO | 2011060095 | 5/2011 |

OTHER PUBLICATIONS

Valles, C. et al. Transgenic Organs and Xenotransplants, LopezLarrea Ed. Springer-Verlag Berlin, pp. 73-88, 2012.*
Pouyani T. et al. Functionalized Derivatives of Hyaluronic Acid Oligosaccharides. Bioconjugate Chem 5:339-347, 1994.*
de Paz J. et al. Exploration of the Use of an Acylsulfonamide Safety Catch Linker for the Polymer Supported Synthesis of Hyaluronic Acid Oligosaccharides. Carbohydrate Research 345:565-571, 2010.*
"European Search Report for EP12382325 dated Oct. 29, 2012".
"International Search Report for PCT/EP2013/066825 dated Oct. 8, 2013".
Amvam-Zollo, et al., "*Streptococcus pneumoniae* Type XIV Polysccharide:Synthesis of a Repeating Branched Tetrasaccharide With Dioxa-Type Spacer-Arms", Carbohydrate Research, 150 (1986) 199-212.
Chernyak, et al., "A New Type of Carbohydrate-Containing Synthetic Anti-gen: Synthesis of Carbohydrate-Containing Poly-Acrylamide Copolymers Having the Specificity of O:3 and O:4 Factors of *Salmonella*", Carbohydrate Research, 128 (1984) 269-282.
Cooper, et al., "Identification of a-galactosyl and other carboydrate epitopes that are bound by human anti-pig antibodies: relevance to discordant xenografting in man", Transplant Immunology 19931; 1: 198-205.
Cozzi, et al., "Characterization of Pigs Transgenic for Human Decay-Accelerating Factor 1", Tansplantation, vol. 64 (10) Nov. 27, 1997, pp. 1383-1392.
Dahmen, et al., "2-Bromoethyl glycosides: applications in the synthesis of spacer-arm glycosides", Carbohydrate Research, 118 (1983) 292-301.
Dahmen, et al., "Synthesis of Spacer-Arm, Lipid, and Ethyl Glycosides of the Trisacharide Portion (a-D-Gal-(1-4)-B-D-Gal-(1-4)-B-D-Glc) of the Blood Group Pk Antigen: Preparation of Neo-Glycoproteins", Carbohydrate Research, 127 (1984) 15-25.

(Continued)

*Primary Examiner* — Ralph Gitomer
(74) *Attorney, Agent, or Firm* — KramerAmado, P.C.

(57) ABSTRACT

The present invention relates to methods for determining the probability of transplant rejection based on the determination in the subject recipient of the transplant of the levels of antibodies specific for hyaluronic acid. The invention relates as well to methods for attenuating transplant rejection and compositions to prevent transplant rejection based on the depletion of anti-hyaluronic acid antibodies from the subject.

15 Claims, 15 Drawing Sheets

(56) References Cited

OTHER PUBLICATIONS

Ekborg, et al., "Synthesis of Three Disaccharides for the Preparation of Immunogens Bearing Immunodeterminants Known to Occur on Glycoproteins", Carbohydrate Research, 110 (1982) 55-67.
Fabrega, et al., "Different Time Course of Circulating Adhesion Molecules and Hyaluran During Hepatic Allograft Rejection", Transplantation, vol. 69, Feb. 27, 2000, pp. 569-573.
Fernadez-Santana, et al., "Glycosides of Monoallyl Diethylene Glycol. A New Type of Spacer Group for Synthetic Oligosaccharides", J. Carbohydrate Chemistry, 8(3), 531-537 (1989).
Garegg, et al., "A Synthesis of 8-Methoxycarbonyloct-1-YL O-a-D-Galactopyranosyl-(1-3)-O-B-D Galactopyranosyl-(1-4)-2-Acetamido-2-deoxy-B-D-Glucopyranoside", Carbohydrate Research, 136 (1985) 207-213.
Huflejt, et al., "anit-carbohydrate antibodies of normal sera: Findings surprises and challenges", Molecular Immunology, 46 (2009) 303-3049.
Johnson, et al., "Can Serum Hyaluronan Predict Endothelial Cell Dysfunction After Liver Transplantation?", Liver Transplantation, Abstract #880, Poster Board # Session: p. 136-II.
Johnsson, et ai., "Serum Hyaluronan—A Potential Marker of Cardiac Allograft Rejection?", Journal of Heart and Lung Transplantation, vol. 25, No. 5, May 1, 2006, pp. 544-549.
Lee, et al., "Synthesis of 3-(2-Aminoethylthio)Propyl Glycosides", Carbohydrate Research, 37 (1974) 193-201.
Mañez, et al., "Removal of bowel aerobic gram-negative bacteria is more effective than immunosuppression with cyclophosphamide and steroids to decrease natural a-Galactosyl IgG antibodies", Xenostransplantation 2001: 8: 15-23.
Maroski, et al "Shear stress increases endothelial hyaluronan synthase 2 and hyaluronan synthesis especially in regard to an atheroprotective flow profile", Exp Physiol 96.9 pp. 977-986.
Obukhova, et al., "Normal human serum contains high levels of anti-Galal-4-GlcNAc antibodies", Xenotransplantation, 2007: 14; 627-635.
Paulsen, et al., "Synthese Von Oligosaccharid-Dertminanten Mit Amid-Spacer Vom TYP Des T-Antigens", Carbohydrate Research, 104(1982) 195-219.
Pungpapong, et al., "Serum Fibrosis Markers Can Predict Rapid Fibrosis Progression After Liver Transplantation for Hepatitis C", Liver Transplantation, 14:1294-1302, 2008.
Rana, et al., "Synthesis of Phenyl 2-Acetamido-2-eoxy-3-O-a-L-Fucopyranosyl-B-D-Glucopyranoside and Related Compounds", Carbohydrate Research, 91 (1981) 149-157.
Schmoeckel, et al "Orthotopic Heart Transplantation in a Transgenic Pig-to Primate Model", Transplantation, vol, 65(12) Jun. 27, 1998, p. 1570-1577.
Von Gunten, et al., "IVIg contains a broad repertoire of anti-carbohydrate antibodies that is not restricted to the IgG2 subclass", J Allergy Clin Immunol. Jun. 2009; 123(6): 1268-76.
Rowe, et al., "Handbook of Pharmaceutical Excipients", Sixth Ed., 2009, pp. 20-22, 159-161, 646-648.
Vanderhooft, "Rheological Properties of Cross-Linked Hyaluronan-Gelatin Hydrogels for Tissue Engineering", Macromol. Biosci. 2009, vol. 9, pp. 20-28.
Beeson, et al., "Adhesion of Plasmodium falciparum-infected erythrocytes to hyaluronic acid in placental malaria", 2000 Natl Med. 6(1): 86-90.
Cozzi, et al., "Long-term survival of nonhuman primates receiving life-supporting transgenic porcine kidney xenografts", 2000 Transplantation 70(1): 15-21 (PubMed).
Cozzi, et al., "Xerotransplantation—current status and future perspectives", 2006 British Medical Bulletin 75&76: 99-114.
Fattal, et al., "An antibody profile of systemic lupus erythematosus detected by antigen microarray", 2010 Immunology 130(3): 337-343.
Holzknecht, et al., "Immune Complex Formation After Xenotransplantation", 2002 Am.J. Pathol. 158(2): 627-637.
Jou, et al., "Biocompatibility and Antibacterial Activity of Chitosan and Hyaluronic Acid Immobilized Polyester Fibers", 2007 J. Appl. Pol. Sci. 104(1): 220-225.
Sun, "Characterization of Chemisorbed Hyaluronic Acid Directly Immobilized on Solid Substrates", 2005 J. Biomed. Mat. Res. 72(2): 292-298.

\* cited by examiner

IMMUNOADSORBENT COMPOSITIONS COMPRISING HYALURONIC ACID OLIGOSACCHARIDES

TECHNICAL FIELD

The present invention relates to the field of immunomodulation and, more in particular, to methods for determining the probability of transplant rejection, methods for attenuating transplant rejection and compositions to prevent transplant rejection, all of them based on the finding that the anti-hyaluronic acid antibody level is increased in subjects suffering transplant rejection.

BACKGROUND ART

A transplant is a complex medical treatment that allows the replacement of diseased organs in an individual, improving his quality of life or even allowing his survival.

Transplant rejection is one of the greatest challenges to transplantation. It is the outcome of the natural response of the immune system to a foreign substance, or antigen. This complex process is mainly T-lymphocyte mediated, although it involves serial interactions between foreign antigens, antibodies, T lymphocytes, macrophages, cytokines (also known as lymphokines or interleukins), adhesion molecules (ie, co-stimulatory molecules), and membrane proteins that enhance binding of T lymphocytes and B lymphocytes.

The goal of immunosuppressive therapy is to prevent and treat transplant rejection as well as to prolong transplant and patient survival. However, due to the potency of immunosupressive agents and inter- and intra-individual variability in pharmacokinetics, dose individualization is required to maintain adequate immunosuppression while minimizing adverse reactions. Poor water solubility and bioavailability contribute to the complexity of dosing immunosuppressive agents such as cyclosporine and sirolimus.

Transplant rejection can be hyperacute (within the first hours after transplantation or during the early days) caused by preformed antibodies, acute (during the early days or months) caused by T-lymphocytes or chronic (months or even years later) mainly caused antibodies. The development of methodologies to predict and/or prevent rejection would increase transplant success.

Due to a worldwide shortage of available human organs for transplantation, xenotransplantation (transplantation of living cells, tissues or organs from one species to another) is a valuable alternative to conventional allotransplantation (same-species transplant). Nonhuman primates were first considered as a potential organ source for xenotransplantation to humans. Chimpanzees were originally considered to be the best option, since their organs are of similar size and they have good blood type compatibility with humans. However, since chimpanzees are listed as an endangered species, other potential donors were sought out. Baboons are more readily available, however they are also not practical as potential donors. Problems include their smaller body size, the infrequency of blood group O (the universal donor), their long gestation period, and that they typically produce few offspring. In addition, a major problem with the use of nonhuman primates is the increased risk of disease transmission, since they are so closely related to humans. Pigs are currently thought to be the best candidates for organ donation. The risk of cross-species disease transmission is decreased because of their increased phylogenetic distance from humans. They are readily available, their organs are anatomically comparable in size, and new infectious agents are less likely since they have been in close contact with humans through domestication for many generations.

In order to overcome hyperacute rejection after xenotransplantation, animal organ/tissues have been engineered for their use in xenotransplantation. An alternative strategy to avoid rejection of xenogeneic cells is disclosed in EP 0661980, which involves removal of xenoantibodies from the blood of the recipient and/or inhibition of xenoantibodies in vivo.

Different markers with a predictive value of transplant rejection have been described in the art. WO2011/119980 discloses methods for determining whether a subject who has received an allograft is undergoing acute rejection that comprise evaluating the level of a plurality of biomarkers, including CD44, EMOD, PEDF in a sample from a subject who has received the allotranplant. US2003175811A1 discloses the use of proteins, such as MLC2, TPM1, troponine C or actin, or antibodies against them as markers for the diagnosis and/or prognosis of acute rejection. Johnson L B et al. shows that serum hyaluronic acid (HA) can detect endothelial cell dysfunction following liver transplantation in patients with rejection, primary non-function or vascular thrombosis, indicating that serum HA may provide a non-invasive measure for early graft function (Johnson L B et al. 2008 American Journal of Transplantation 3 (Suppl 5): 378). Fábrega E et al. shows that the release of circulating adhesion molecules is a prominent feature coinciding with the first episode of hepatic rejection, and that hyaluronan levels may be a sensitive marker of liver endothelial cell function in the postoperative period of liver transplantation (Fábrega E et al. 2000 Transplantation 69:569-573).

Thus, there is a need in the state of the art to identify reliable alternative markers and/or predictors for allotransplant and/or xenotransplant rejection in order to overcome the problems associated to transplant rejection and to improve the overall survival of patients undergoing transplantation.

BRIEF SUMMARY OF THE INVENTION

The present invention relates to methods for determining the probability of transplant rejection in a subject based on the levels of anti-hyaluronic acid antibodies, compositions for attenuating transplant rejection, immunoabsorbent compositions for removing preformed antibodies and blood to be infused to a subject recipient of a transplant.

In a first aspect, the present invention relates to a method for determining the probability of transplant rejection in a subject who has been subjected to transplantation that comprises determining in a sample from said subject the levels of antibodies specific for at least one hyaluronic acid oligosaccharide, wherein if the levels of antibodies specific for at least one hyaluronic acid oligosaccharide are modified when compared to a reference value, then there is a high probability of transplant rejection in said subject.

In a second aspect, the invention relates to an immunoabsorbent composition comprising hyaluronic acid oligosaccharides attached to a biocompatible solid support comprising attached thereto.

In a further aspect, the invention relates to an immunoabsorbent composition as above for use in a method of attenuating antibody-mediated transplant rejection in a subject recipient of a transplant.

In a further aspect, the invention relates to a polymeric structure comprising a polymeric backbone wherein one or more of the monomer units forming the polymeric backbone are linked to a hyaluronic acid oligosaccharide.

In a further aspect, the invention relates to a polymeric structure as above for use in a method for attenuating antibody-mediated transplant rejection in a subject recipient of a transplant.

In a further aspect, the invention relates to a cell population which stably incorporate exogenous hyaluronic acid oligosaccharides in their surface.

In a further aspect, the invention relates to a cell population as above for use in a method for attenuating antibody-mediated transplant rejection in a subject recipient of a transplant.

In a further aspect, the invention relates to a hyaluronic acid oligosaccharide for use in a method for attenuating antibody-mediated transplant rejection in a subject recipient of a transplant.

In a further aspect, the invention relates to blood or plasma or serum useful for infusing into a subject recipient of a transplant to attenuate transplant rejection, the blood or plasma being depleted of antibodies to hyaluronic acid oligosaccharides.

In a further aspect, the invention relates to blood or plasma or serum as above for use in a method for attenuating antibody-mediated transplant rejection in a subject recipient of a transplant.

In a last aspect, the invention relates to a method for diagnosing systemic lupus erythematosus (SLE) in a subject comprising determining in a sample from said subject the levels of antibodies specific for at least one hyaluronic acid oligosaccharide, wherein if the levels of antibodies specific for said at least one hyaluronic acid oligosaccharide are modified with respect to a reference value, then the subject is diagnosed with SLE.

DETAILED DESCRIPTION OF THE INVENTION

Figure 1:
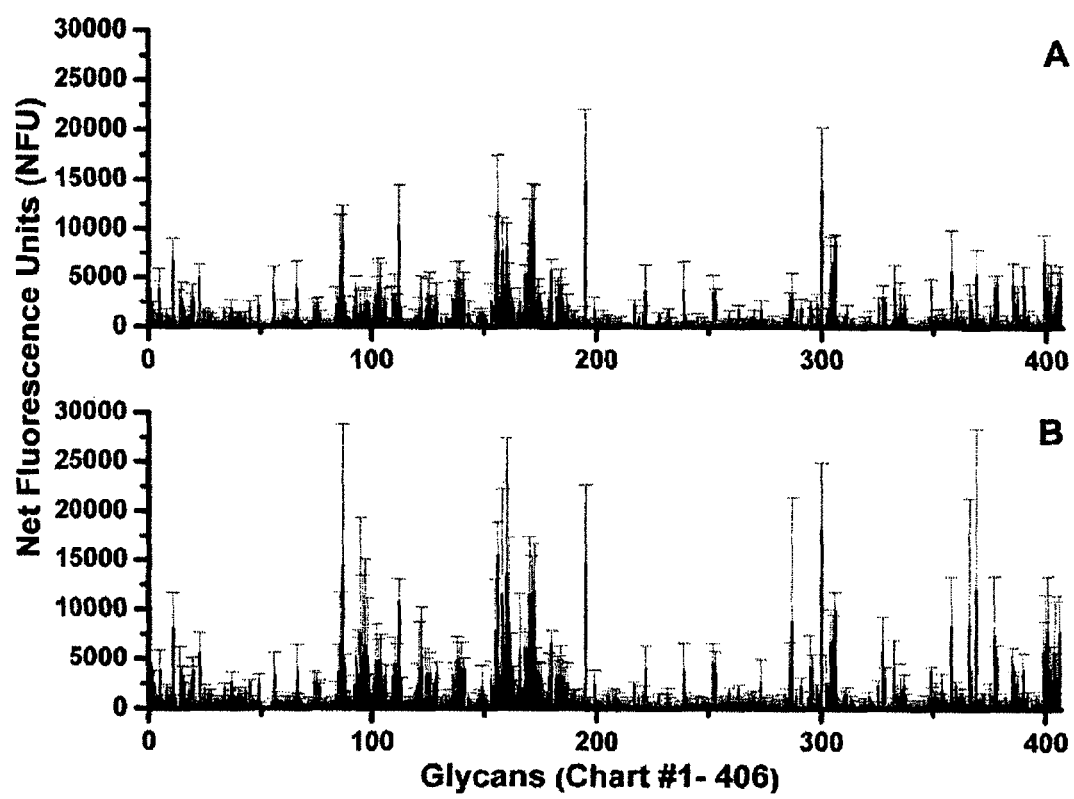
FIG. 1 shows the levels of anti-carbohydrate antibodies bound to glycan array in non-human primates before xenotransplantation of a pig organ (A) and at acute humoral xenotransplant rejection (AHXR) (B). Results represent the mean and standard deviation (S.D.) of the five experiments.

The authors of the present invention have analyzed the pattern of anti-carbohydrate antibodies in a non-human primate model subjected to xenotransplantation of pig organs or to exposure to pig red blood cells (PRBC) by using a glycan array of 406 glycans. The authors have observed significant changes in the serum levels of antibodies specific for hyaluronic acid oligosaccharides as a result of acute humoral rejection to xenotransplantation. Injection of pig red blood cells, which do not express hyaluronic acid, also resulted in increased levels of anti-HA disaccharide antibodies, showing that the hyaluronic antigen has a host origin. The existence of natural anti-HA disaccharide antibodies in human and non-human primates is particularly relevant, since these antibodies are not found in models such as rats, mice or rabbits.

Humans and non-human primates have natural (preformed) antibodies against hyaluronic acid (HA). The authors of the present invention have detected the presence of preformed anti-HA disaccharide, anti-HA tetrasaccharide and anti-HA decasaccharide antibodies in humans, as well as anti-HA IgM antibodies in rats immunized with PRBC and hamster blood.

The authors have also identified HA tetra- and hexasaccharides as antigens involved in the reactivity of the xeno-antibodies.

Lastly, the inventors have also shown that patients with Systemic Lupus Erythematosus (SLE) show decreased levels of IgM antibodies against hyaluronic acid disaccharides and increased levels of IgG antibodies against hyaluronic acid disaccharides.

DEFINITIONS

The terms "antibody," "immunoglobulin," and the like terms refer to a polypeptide substantially encoded by an immunoglobulin gene or immunoglobulin genes, or fragments thereof, which specifically bind and recognize an analyte (antigen). The recognized immunoglobulin genes include the kappa, lambda, alpha, gamma, delta, epsilon and mu constant region genes, as well as the myriad immunoglobulin variable region genes. Light chains are classified as either kappa or lambda. Heavy chains are classified as gamma, mu, alpha, delta, or epsilon, which in turn define the immunoglobulin classes, IgG, IgM, IgA, IgD, and IgE, respectively. An exemplary immunoglobulin (antibody) structural unit is composed of two pairs of polypeptide chains, each pair having one "light" (about 25 kD) and one "heavy" chain (about 50-70 kD). The N-terminus of each chain defines a variable region of about 100 to 110 or more amino acids primarily responsible for antigen recognition. The terms variable light chain (VL) and variable heavy chain (VH) refer to these light and heavy chains respectively. The C-terminal ends of each heavy chain are disulfide bonded together, and form the constant region of the antibody. Depending on the amino acid sequence of the constant domain of their heavy chains, antibodies can be assigned to different "classes". There are five-major classes of antibodies: IgA, IgD, IgE, IgG, and IgM, and several of these may be further divided into "subclasses" (isotypes), e.g., IgG1, IgG2, IgG3, IgG4, IgA, and IgA2. Full-length immunoglobulin "light chains" (of about 25 kDa or about 214 amino acids) comprise a variable region of about 110 amino acids at the NH2-terminus and a kappa or lambda constant region at the COOH-terminus. Full-length immunoglobulin "heavy chains" (of about 50 kDa or about 446 amino acids) similarly comprise a variable region (of about 116 amino acids) and one of the aforementioned heavy chain constant regions or classes, e.g., gamma (of about 330 amino acids). The subunit structures and three-dimensional configurations of different classes of immunoglobulins are well known.

In the context of the invention, the antigen that is recognized and can be targeted by the antibody is a carbohydrate and, in particular, a hyaluronic acid oligosaccharide, and the antibody is an anti-hyaluronic acid antibody that binds specifically to hyaluronic acid. In a preferred embodiment of the invention, the antibody is an antibody specific for an anti-hyaluronic acid oligosaccharides comprising hyaluronic acid. In a more preferred embodiment of the invention, the anti-hyaluronic acid antibody is an antibody specific for hyaluronic acid disaccharides, tetrasaccharides, hexasaccharides and/or decasaccharides. As used herein, the expression "an antibody targets" is referred to the specific recognition and binding of the antibody to a particular antigen. As it is used herein, the expression "binds specifically to" refers to the capacity of the antibodies for binding specifically to hyaluronic acid and not to other carbohydrates.

The term "HA oligosaccharide", as used herein, refers to any oligosaccharide which comprises at least one disaccharide unit of hyaluronan. The disaccharide unit of hyaluronan has the following formula (formula I):

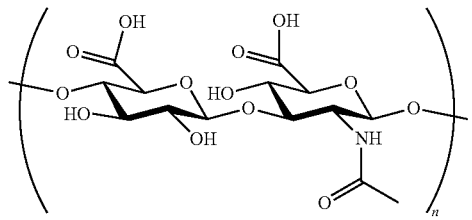

The term "hyaluronic acid", "hyaluronan" or "hyaluronate" or "HA" relates to an anionic, nonsulfated glycosaminoglycan which is a polymer of disaccharide repeating units, themselves composed of D-glucuronic acid and D-N-acetylglucosamine (GlcAβ1-3GlcNAcβ), linked via alternating β-1,4 and β-1,3 glycosidic bonds. Hyaluronan can be 25,000 disaccharide repeats in length. Polymers of hyaluronan can range in size from 5,000 to 20,000,000 Da in vivo. The average molecular weight in human synovial fluid is 3-4 million Da, and hyaluronan purified from human umbilical cord is 3,140,000 Da.

In a particular embodiment of the invention, the HA oligosaccharide are oligosaccharides according to the previous formula I, wherein $2 \leq n \leq 20$. In a preferred embodiment, the HA oligosaccharides are disaccharides (n=1), tetrasaccharides (n=2), hexasaccharides (n=3), and decasaccharides (n=5). The anti-hyaluronic acid antibodies of the present invention are antibodies targeting oligosaccharides comprising hyaluronic acid. In a preferred embodiment, the anti-hyaluronic acid antibodies of the present invention are antibodies targeting hyaluronic acid disaccharides, tetrasaccharides and/or decasaccharides.

The term "antibody specific for a hyaluronic acid oligosaccharide", as used herein, refers to antibodies which are capable of specifically binding to a given HA oligosaccharide (e.g. a HA disaccharide) without showing specific binding to oligosaccharides of different composition.

The term "diagnosis", as used herein, refers both to the process of attempting to determine and/or identify a possible disease in a subject, i.e. the diagnostic procedure, and to the opinion reached by this process, i.e. the diagnostic opinion. As such, it can also be regarded as an attempt at classification of an individual's condition into separate and distinct categories that allow medical decisions about treatment and prognosis to be made. As the person skilled in the art will understand, such a diagnosis may not be correct for 100% of the subject to diagnose, although preferred it is. The term however requires that can identify a statistically significant proportion of subject suffering from such pathologies (in this case, SLE). The skilled in the art may determine whether a party is statistically significant using different statistical evaluation tools well known, for example, by determination of confidence intervals, the p-value determination, Student's-test, the Mann-Whitney, etc. (see Dowdy and Wearden, 1983). Preferred confidence intervals are at least, 50%, at least 60%, at least 70%, at least 80%, at least 90% or at least 95%. The p-values are preferably, 0.05, 0.025, 0.001 or lower. The term "non-human primate" is referred to any primate except of humans and comprises, without being limited to, monkeys such as spider monkeys, squirrel monkeys, marmosets, baboons and relatives and great apes such as gorillas, orangutans, gibbons, siamangs, chimpanzees and relatives.

The term "prediction" as used herein, refers to the determination of the likelihood that the subject in need of a transplant and who has received said transplant will suffer rejection after transplantation.

The term "rejection" is used in the present invention in a context of cell/tissue/organ transplant, and is related to the process by which a transplantated cell, tissue and/or organ is rejected by the immune system of the recipient, which destroys the transplanted cell, tissue and/or organ. Different categories of rejection can be distinguised: hyperacute rejection (HAR, also known as accelerated humoral rejection or ACHR), acute rejection (also known as cellular rejection) and chronic rejection.

Hyperacute rejection (HAR) or accelerated humoral rejection (ACHR), with onset within minutes of anastomosis of blood supply, is caused by circulating antibodies; the kidneys are soft, cyanotic with stasis of blood in the glomerular capillaries, segmental thrombosis, necrosis, fibrin thrombi in glomerular tufts, interstitial hemorrhage, leukocytosis and sludging of PMNs and platelets, erythrocyte stasis, mesangial cell swelling, deposition of IgG, IgM, C3 in arterial walls. It occurs within minutes or hours after transplant and it is initiated by preexisting humoral immunity, due to pre-existing antibodies directed to components of the transplant. It is observed typically after xenotransplantation, in rare instances (such as ABO incompatibility) is observed after allotransplantation. If tissue is left implanted, systemic inflammatory response syndrome occurs. In the context of the invention, hyperacute rejection is considered to occur at least 1 hour, 2 hours, 3 hours, 4 hours, 5 hours, 6 hours, 7 hours, 8 hours, 9 hours, 10 hours, 11 hours, 12 hours, 13 hours, 14 hours, 15 hours, 16 hours, 17 hours, 18 hours, 19 hours, 20 hours, 21 hours, 22 hours, 23 hours, 1 day, or 2 days after transplantation.

Humoral rejection (also referred herein to as "antibody-mediated rejection" or ABMR) includes hyperacute rejection (HAR) and is a type of rejection characterized by acute allograft injury that is resistant to potent anti-T cell therapy, by the detection of circulating donor specific antibodies, and the deposition of complement components in the graft. ABMR with elevated circulating alloantibodies and complement activation that occurs in 20-30 percent of acute rejection cases has a poorer prognosis than cellular rejection.

Acute rejection, with onset 2-60 days after transplantation, is characterized by interstitial vascular endothelial cell swelling, interstitial accumulation of lymphocytes, plasma cells, immunoblasts, macrophages, neutrophils; tubular separation with edema/necrosis of tubular epithelium; swelling and vacuolization of the endothelial cells, vascular edema, bleeding and inflammation, renal tubular necrosis, sclerosed glomeruli, tubular 'thyroidization', creatinine clearance, malaise, fever, HTN, oliguria. The acute rejection occurs to some degree in all transplants, except between identical twins, unless immunosuppression is achieved (usually through drugs). Acute rejection begins as early as one week after transplant, the risk highest in the first three months, though it can occur months to years later. Highly vascular tissues such as kidney or liver often host the earliest signs—particularly at endothelial cells lining blood vessels—though it eventually occurs in roughly 10 to 30% of kidney transplants, and 50 to 60% of liver transplants. Generally, acute rejection can be inhibited or suppressed with immunosuppressive drugs such as rapamycin, cyclosporin A, anti-CD40L monoclonal antibody and the like. In the context of the invention, acute rejection is considered to occur at least 3 days, 4 days, 5 days, 6 days, 7 days, 8 days, 9 days, 10 days, 11 days, 12 days, 13 days, 14 days, 15 days, 1 month, 2 months, 3 months or 6 months after transplantation.

Chronic rejection has a late onset, often more than 60 days after transplantation, and frequently accompanied by acute changes superimposed, increased mesangial cells with myointimal proliferation and crescent formation; mesangioproliferative glomerulonephritis, and interstitial fibrosis; there is in general a poor response to corticosteroids. It occurs in humans within several months to years after engraftment, even in the presence of successful immunosuppression of acute rejection. Fibrosis is a common factor in chronic rejection of all types of organ transplants. Chronic rejection can typically be described by a range of specific disorders that are characteristic of the particular organ. For example, in lung transplants, such disorders include fibroproliferative destruction of the airway (bronchiolitis obliterans); in heart transplants or transplants of cardiac tissue, such as valve replacements, such disorders include fibrotic atherosclerosis; in kidney transplants, such disorders include, obstructive nephropathy, nephrosclerorsis, tubulointerstitial nephropathy; and in liver transplants, such disorders include disappearing bile duct syndrome. Chronic rejection can also be characterized by ischemic insult, denervation of the transplanted tissue, hyperlipidemia and hypertension associated with immunosuppressive drugs. In the context of the invention, chronic rejection is considered to occur months after transplantation. In a preferred embodiment of the invention, chronic rejection is considered to occur at least 2 months, at least 3 months, at least 4 months, at least 5 months or at least 6 months after transplantation.

The term "rodent" is used to refer to any mammal of the order Rodentia and includes, without limitation, the following species: mouse, rat, squirrel, chipmunk, gopher, porcupine, beaver, hamster, gerbil, guinea pig, degu, chinchilla, prairie dog, and groundhog.

The term "sample" as used herein, relates to a biofluid sample that can be obtained from a subject. In a preferred embodiment of the invention, the biofluid is any fluid of the body comprising antibodies. In a more preferred embodiment of the invention, the biofluid is selected from blood (such as peripheral blood), serum or plasma. In a more preferred embodiment of the methods of the invention, the sample is serum or plasma. The blood sample is typically extracted by means of puncturing an artery or vein, normally a vein from the inner part of the elbow or from the back of the hand, the blood sample being collected in a air-tight vial or syringe. A capillary puncture normally on the heel or on the distal phalanxes of fingers can be performed for analysis by means of a micromethod. Serum can be obtained from the complete blood sample and in the absence of anticoagulant by leaving the sample to settle for 10 minutes so that it coagulates and subsequently centrifuging it at 1,500 rpm for 10 minutes for the purpose of separating the cells (precipitate) from the serum (supernatant). In turn, to obtain the plasma sample the complete blood is contacted with an anticoagulant and is centrifuged at 3,000 rpm for 20 minutes. The precipitate of said centrifugation corresponds to the formed elements, and the supernatant corresponds to the plasma. The serum or the plasma obtained can be transferred to a storage tube for sample analysis by means of the methods of the invention.

In the context of the present invention, the term "transplant rejection" comprises hyperacute, acute and chronic transplant rejection. In a preferred embodiment of the invention, the transplant rejection is acute humoral rejection.

The term "subject" or "individual" or "animal" or "patient" or "mammal," is meant any subject, particularly a mammalian subject, for whom diagnosis, prognosis, or therapy is desired. Mammalian subjects include humans, domestic animals, farm animals, and zoo, sports, or pet animals such as dogs, cats, guinea pigs, rabbits, rats, mice, horses, cattle, cows, and so on. In a preferred embodiment of the invention, the subject is a mammal. In a more preferred embodiment of the invention, the subject is a human or a non-human primate. In accordance with the present invention, the donor and/or the recipient of the transplant is a mammal. In one embodiment, at least the recipient is human. The donor may be alive or deceased at the time the graft is removed.

The term "systemic lupus erythematosus" or SLE, as used herein, relates to an immune system disease that typically causes harm to the skin, joints, kidneys, and brain.

The term "transplantation" refers to a surgical procedure by which a cell, tissue or organ is transferred from a donor subject to a recipient subject or from one part of the body to another in the same subject. The "donor subject" is the subject who gives blood, cells, tissues, or an organ for another subject by blood transfusion or an organ transplant. In the context of the invention, the donor subject gives cell(s), tissue(s) and/or organ(s) to a recipient subject. According to the invention, the donor subject is a human or another mammal. The "recipient subject" is the subject who receives blood, cells, tissues, or an organ from another subject by blood transfusion or an organ transplant. In the context of the invention, the recipient subject receives tissue(s) and/or organ(s) from a donor subject. According to the invention, the recipient subject is a human or another mammal Transplanted tissues comprise, but are not limited to, bone tissue, tendons, corneal tissue, heart valves, veins and bone marrow. Transplanted organs comprise, but are not limited to, heart, lung, liver, kidney, pancreas and intestine. The particular surgical procedure of transplantation wherein the donor subject and the recipient subject are genetically non-identical members of the same species is known as allotransplantation. Thus, the term allotransplant (also known as allograft, allogeneic transplant or homograft) is related to the transplantation of cells, tissues or organs sourced from a genetically non-identical member of the same species as the recipient. The term "allotransplantable" refers to organs or tissues that are relatively often or routinely transplanted. Examples of allotransplantable organs include heart, lung, liver, pancreas, kidney and intestine. The particular surgical procedure of transplantation wherein the donor subject and the recipient subject are members of different species is known as xenotransplantation. Thus, the term xenotransplant (also known as xenograft, xenogeneic transplant or heterograft) is related to the transplantation of cells, tissues or organs sourced from a donor to a recipient, wherein donor and recipient are members of different species.

Method for Determining the Probability of Transplant Rejection (First Method of the Invention)

In a first aspect, the invention relates to a method for determining the probability of transplant rejection in a subject who has been subjected to transplantation that comprises determining in a sample from said subject the levels of antibodies specific for at least an hyaluronic acid oligosaccharide, wherein if the levels of antibodies specific for the hyaluronic acid oligosaccharide are modified with respect to a reference value, then there is a high probability of transplant rejection in said subject.

In a first step, the first method of the invention comprises the determination of the levels of antibodies specific for at least an hyaluronic acid oligosaccharide in a sample from a subject who has been subjected to transplantation.

The levels of antibodies specific for at least an hyaluronic acid oligosaccharide can be determined by any method suitable for determination of antibody levels or antibody titer of antibodies with a desired specificity known by the skilled in the art and include, but are not limited to, immunochemical assays such as ELISA (Enzyme-Linked Immuno Sorbent Assay), immunostaining, immunochemical assays, immunofluorescence, flow cytometry, Western blot, radioimmunoassays, immunohistochemical assays and immunoprecipitations. By way of non-limiting example, the levels of anti-hyaluronic acid antibodies can be quantified by means of secondary antibodies with a capacity to specifically bind to anti-hyaluronic acid antibodies (or to fragments thereof) and subsequent quantification of the resulting anti-hyaluronic acid antibody-secondary antibody complexes. The antibodies to be employed in these assays can be, for example, polyclonal sera, hybridoma supernatants or monoclonal antibodies, antibody fragments, Fv, Fab, Fab' y F(ab')2, ScFv, diabodies, triabodies, tetrabodies and humanised antibodies. At the same time, the antibodies can be labeled or not. Illustrative, but non-exclusive examples of markers which can be used include radioactive isotopes, enzymes, fluorophores, chemiluminescent reagents, enzymatic substrates or cofactors, enzymatic inhibitors, particles, colorants, etc. There are a wide variety of well-known assays that can be used in the present invention, which use non-labeled antibodies (primary antibody) and labeled antibodies (secondary antibodies); among these techniques are included Western-blot or Western transfer, ELISA (enzyme linked immunosorbent assay), RIA (radioimmunoassay), competitive EIA (enzymatic immunoassay), DAS-ELISA (double antibody sandwich ELISA), immunocytochemical and immunohistochemical techniques, techniques based on the use of biochips or microarrays including specific antibodies or assays based on colloidal precipitation in formats such as dipsticks. Other ways of detecting and quantifying the anti-hyaluronic acid antibodies include techniques of affinity chromatography, binding-ligand assays, etc.

In a preferred embodiment of the invention, the levels of antibodies specific for at least one hyaluronic acid oligosaccharide are determined in a sample from a subject who has been subjected to transplantation by means of ELISA or immunohistochemistry. In the ELISA, plates are coated with hyaluronic oligosaccharides including, but not limited to, HA disaccharide, HA tetrasaccharide, HA hexasaccharide and/or HA decasaccharide. The HA oligosaccharide can be linked to a protein, such as human serum albumin, or conjugated to polyacrilamide or sepharose. Alternatively, specific antibodies against hyaluronic acid oligosaccharides (including, without being limited to, disaccharide, tetrasaccharide, hexasaccharide and decasaccharide) are used. Hyaluronic acid antibodies are commercially available and include, without being limited to, the polyclonal anti-HA ab53842 antibody for human and mouse HA from Abcam, the polyclonal sheep anti-human HA MBS220936 antibody from MyBioSource and the sheep anti-human HA BP549 antibody from Acris Antibodies In a preferred embodiment, the antibodies specific for at least one hyaluronic acid oligosaccharide which are determined according to the first method of the invention are selected from the group consisting of one or more of IgA, IgD, IgE, IgG, and IgM. In another embodiment, the antibody to be detected is an IgG antibody which belongs to one or more of the IgG1, IgG2, IgG3, IgG4, IgA, and IgA2 isotype.

In a preferred embodiment, the antibodies which are determined in the method according to the present invention are selected from the group consisting of IgM antibodies against HA disaccharide, IgM antibodies against the HA tetrasaccharide, IgM antibodies against the HA hexasaccharides, IgM antibodies against the HA decasaccharides, IgG antibodies against HA disaccharide, IgG antibodies against the HA tetrasaccharides, IgG antibodies against the HA hexasaccharides and/or IgG antibodies against the HA decasaccharides.

The levels of antibodies specific for at least one hyaluronic acid oligosaccharide in a sample from a subject who has been subjected to transplantation can be determined at different time points after transplantation. In an embodiment of the invention, the levels can be determined 1 hour, 2 hours, 3 hours, 4 hours, 5 hours, 6 hours, 7 hours, 8 hours, 9 hours, 10 hours, 11 hours, 12 hours, 13 hours, 14 hours, 15 hours, 16 hours, 17 hours, 18 hours, 19 hours, 20 hours, 21 hours, 22 hours, 23 hours, 1 day or 2 days after transplantation. In another embodiment of the invention, the levels can be determined 3 days, 4 days, 5 days, 6 days, 7 days, 8 days, 9 days, 10 days, 11 days, 12 days or 13 days after transplantation. In another embodiment of the invention, the levels of antibodies specific for at least one hyaluronic acid oligosaccharide can be determined 2 weeks, 3 weeks, 1 month, 2 months, 3 months, 4 months, 5 months or 6 months after transplantation.

In a second step, the first method of the invention comprises comparing the level of antibodies specific for at least one hyaluronic acid oligosaccharide as determined in the first step to a reference value, wherein if the levels of antibodies specific for at least one hyaluronic acid oligosaccharide in said sample are modified when compared to a reference value, then there is a high probability of transplant rejection in said subject subjected to a transplant.

The term "modified" or "substantially modified" refers to an increase or a decrease in the levels of antibodies specific for at least one hyaluronic acid oligosaccharide in a sample from a subject who has been subjected to transplantation when compared to a reference value.

In particular, an increase in the levels of antibodies specific for at least one hyaluronic acid oligosaccharide with respect to the reference value of at least 1.1-fold, 1.5-fold, 5-fold, 10-fold, 20-fold, 30-fold, 40-fold, 50-fold, 60-fold, 70-fold, 80-fold, 90-fold, 100-fold or even more compared with the reference value is considered as "increased" levels. On the other hand, a decrease in the levels of antibodies specific for at least one hyaluronic acid oligosaccharide with respect to the reference value of at least 0.9-fold, 0.75-fold, 0.2-fold, 0.1-fold, 0.05-fold, 0.025-fold, 0.02-fold, 0.01-fold, 0.005-fold or even less compared with reference value is considered as "decreased" levels. A "lack of change" in the levels of antibodies specific for at least one hyaluronic acid oligosaccharide with respect to a reference value refers to levels which are substantially unaltered with respect to the reference value. For instance, a lack of change in the levels of antibodies specific for at least one hyaluronic acid oligosaccharide in the sample under study is considered when the levels differ by no more than 0.1%, no more than 0.2%, no more than 0.3%, no more than 0.4%, no more than 0.5%, no more than 0.6%, no more than 0.7%, no more than 0.8%, no more than 0.9%, no more than 1%, no more than 2%, no more than 3%, no more than 4%, no more than 5%, no more than 6%, no more than 7%, no more than 8%, no more than 9%, no more than 10% or no more than the percentage value that is the same as the error associated to the experimental method used in the determination.

In a particular embodiment, the level of antibodies specific for at least one hyaluronic acid oligosaccharide in a subject who has been subjected to transplantation is determined in a sample from said subject that has been obtained 3 days, 4 days, 5 days, 6 days, 7 days, 8 days, 9 days or 10 days after transplantation. In a preferred embodiment of the invention, the level of antibodies specific for at least one hyaluronic acid oligosaccharide in a subject who has been subjected to transplantation is determined in a sample from said subject obtained 3 days, 4 days, 5 days or 6 days after transplantation.

The term "reference value" relates to the level of antibodies specific for at least one hyaluronic acid oligosaccharide in a sample from a subject who will be subjected to transplantation, wherein said sample is obtained from said subject prior to being subjected to transplantation. The sample wherein the level of antibodies specific for at least one hyaluronic acid oligosaccharide is determined as reference value of anti-hyaluronic acid antibody can be obtained 1 hour, 2 hours, 5 hours, 12 hours, 1 day, 2 days, 5 days, 10 days, 20 days, 1 month, 2 months, 6 months or 1 year before the subject is subjected to transplantation. In a preferred embodiment, the sample wherein the level of antibodies specific for at least one hyaluronic acid oligosaccharide is determined as reference value of anti-hyaluronic acid antibody is obtained 1 hour, 2 hours, 5 hours, 12 hours, 1 day or 2 days before the subject is subjected to transplantation.

Once this reference value is established, the level of antibodies specific for at least one hyaluronic acid oligosaccharide in a subject who has been subjected to transplantation can be compared with this reference value, and thus be assigned a "low" or "decreased" level of antibodies specific for at least one hyaluronic acid oligosaccharide if it is under this reference value, or a level of "high" or "increased" level of antibodies specific for at least one hyaluronic acid oligosaccharide if it is above this reference value.

In particular, an "increase" of the level of antibodies specific for at least one hyaluronic acid oligosaccharide when compared to the reference value of at least 1.1-fold, 1.5-fold, 5-fold, 10-fold, 20-fold, 30-fold, 40-fold, 50-fold, 60-fold, 70-fold, 80-fold, 90-fold, 100-fold or even more compared with the reference value is considered as "increased" levels of anti-hyaluronic acid antibody. A "decrease" of the level of antibodies specific for at least one hyaluronic acid oligosaccharide when compared to the reference value of at least 0.9-fold, 0.75-fold, 0.2-fold, 0.1-fold, 0.05-fold, 0.025-fold, 0.02-fold, 0.01-fold, 0.005-fold or even less compared with reference value is considered as "decreased" levels of antibodies specific for at least one hyaluronic acid oligosaccharide.

Once a comparison between the levels of antibodies specific for at least one hyaluronic acid oligosaccharide in a sample from a subject who has been subjected to transplantation and the reference value has been made, the first method of the invention allows determining the probability of transplant rejection in a subject, wherein if the levels of antibodies specific for at least one hyaluronic acid oligosaccharide are modified when compared to a reference value, then there is a high probability of transplant rejection in said subject.

In a particular embodiment of the invention, if the determination of the levels of the antibodies specific for a hyaluronic acid oligosaccharide in the sample from the subject is carried out 1 day or 2 days after being subjected to transplantation, then a decrease in the levels of said antibodies when compared to a reference value is indicative of a high probability of transplant hyperacute rejection in said subject.

In another particular embodiment of the invention, if the determination of the levels of the antibodies specific for a hyaluronic acid oligosaccharide in the sample from the subject is carried out at least 3 days after being subjected to transplantation, then an increase in the levels of antibodies specific for hyaluronic acid oligosaccharide is indicative of a high probability of acute humoral rejection of the transplant in said subject.

In another particular embodiment, if the determination of the levels of the antibodies specific for a hyaluronic acid oligosaccharide in the sample from the subject is carried out at least 2 months after being subjected to transplantation, then an increase in the levels of antibodies specific for hyaluronic acid oligosaccharide is indicative of a high probability of chronic transplant rejection in said subject.

According to the first method of the invention, the levels of anti-hyaluronic acid antibodies are determined in a sample of a subject who has been subjected to transplantation.

In a particular embodiment, the transplant is a xenotransplant or an allotransplant.

In a particular embodiment, the antibodies specific for at least one hyaluronic acid oligosaccharide are antibodies targeting hyaluronic acid disaccharides, hyaluronic acid tetrasaccharides, hyaluronic acid hexasaccharides and/or hyaluronic acid decasaccharides.

In a particular embodiment, the sample is selected from the group consisting of blood, serum and plasma. In a preferred embodiment, the sample is a blood sample.

In a particular embodiment, the subject who has been subjected to transplantation is a mammal. In another embodiment, the mammal is a primate. In preferred embodiments, the primate is a non-human or a human primate. In another particular embodiment of the invention, the subject who has been subjected to transplantation receives an immunosuppressive therapy. The immunosuppressive therapy can be administered to the subject who has been subjected to transplantation before transplantation, after transplantation of before and after transplantation. Immunosuppresive agents commonly used in therapy in transplantation include, but are not limited to, monoclonal antibodies such as baxilimab (Simulect®), daclilzumab (Zenapax®) or muromonab-CD3 (Orthoclone OKT3®), polyclonal antibodies such as antithymocyte immunoglobulin rabbit (Thymoglobulin®) or antithymocyte immunoglobulin equine (AT-GAM®, Lymphoglobulin®), corticosteroids such as methylprednisolone, prednisone or prednisolone, calcineurin inhibitors such as cyclosporine (Neoral®, Sandimmune®) or tacrolimus (Prograf®), mTOR inhibitors such as sirolimus (Rapamune®) or everolimus (Certican®), antiproliferative agents such as azathioprine (Imuran®), purine synthesis inhibitors such as mycophenolate mofetil (CellCept®) or mycophenolate sodium (Myfortic®), alkylating agents such as cyclophosphamide, nitrosureas or platinum compounds, folic acid analogues such as methotrexate, purine analogues such as azathioprine or mercaptopurine, pyrimidine analogues, protein synthesis inhibitors and cytotoxic antibiotics such as dactinomycin, anthracycline, mitomycin C, bleomycin or mithramycin. The immunosuppressive therapy can be administered to the subject who has been subjected to transplantation before transplantation, after transplantation of before and after transplantation. In another particular embodiment of the invention, the subject who has been subjected to transplantation receives a therapy to deplete anti-αGal (Galα1-3Galβ1-4GlcNAc) antibodies. The therapy to deplete anti-αGal antibodies can be administered to the subject who has been subjected to transplantation before transplantation, after transplantation of before and after transplantation. Agents to deplete anti-αGal antibodies include, but are not limited to, the αGal analog GAS914.

Immunosorbent Composition of the Invention for Attenuating Rejection and Uses Thereof In a further aspect, the invention relates to an immunoabsorbent composition useful removing antibodies from a fluid of a subject recipient of a transplant to attenuate transplant rejection by the recipient comprising a biocompatible solid support comprising hyaluronic acid attached thereto.

Supports to which the hyaluronic acid oligosaccharides are attached thereto may be in form of sheets or particles. A large variety of biocompatible solid support materials are known in the art. Non-limiting examples thereof are silica, synthetic silicates such as porous glass, biogenic silicates such as diatomaceous earth, silicate-containing minerals such as kaolinite and synthetic polymers such as polystyrene, polypropylene and polysaccharides.

In a preferred embodiment, the hyaluronic acid oligosaccharide forming part of the immunoabsorbent composition is selected from the group consisting of a hyaluronic acid disaccharide, a hyaluronic acid tetrasaccharide, a hyaluronic acid hexasaccharide and/or a hyaluronic acid decasaccharide.

The solid supports to which the antigens are bound may be in the form of a continuous large surface or in the form of particles. A large variety of biocompatible solid support materials are known in the art. Examples thereof are silica, synthetic silicates such as porous glass, biogenic silicates such as diatomaceous earth, silicate-containing minerals such as kaolinite, and synthetic polymers such as polystyrene, polypropylene, and polysaccharides. Preferred supports are described in U.S. patent application Ser. No. 07/270,950.

The antigen(s) is covalently bound or noncovalently (passively) adsorbed onto the solid support. The covalent bonding may be via reaction between functional groups on the support and the compatible linker arm of the antigen. Linking moieties that are used in indirect bonding are preferably organic bifunctional molecules of appropriate length (at least one carbon atom) which serve simply to distance the antigen from the surface of the solid support.

Numerous aglycon linking arms are known in the art. For example, a linking arm comprising a para-nitrophenyl group (i.e., $-YR=-OC_6H_4pNO_2$) has been disclosed by Ekberg et al. (1982 Carbohydr Res 110: 55-67). At the appropriate time during synthesis, the nitro group is reduced to an amino group which can be protected as N-trifluoroacetamido. Prior to coupling to a support, the trifluoroacetamido group is removed thereby unmasking the amino group.

A linking arm containing sulfur is disclosed by Dahmen et al. (1983 Carbohydr Res 118: 292-301). Specifically, the linking arm is derived from a 2-bromoethyl group which, in a substitution reaction with thionucleophiles, has been shown to lead to linking arms possessing a variety of terminal functional groups such as $-OCH_2CH_2SCH_2CO_2CH_3$ and $-OCH_2CH_2SC_6H_4-pNH_2$.

Rana et al. (1981 Carbohydr Res 91: 149-157) discloses a 6-trifluoroacetamido-hexyl linking arm ($-O-(CH_2)_6-NHCOCF_3$) in which the trifluoroacetamido protecting group can be removed unmasking the primary amino group used for coupling.

Other exemplification of known linking arms include the 7-methoxycarbonyl-3,6,dioxaheptyl linking arm ($-OCH_2-CH_2)_2OCH_2CO_2CH_3$) (Amvam-Zollo et al. 1986 Carbohydr Res 150: 199-212); the 2-(4-methoxycarbonylbutancarboxamido)ethyl ($-OCH_2CH_2NHC(O)(CH_2)_4 CO_2CH_3$) (Paulsen et al. 1982 Carbohydr Res 104: 195-219); the allyl linking arm ($-OCH_2CH=CH_2$) (Chernyak et al. 1984 Carbohydr Res 128: 269-282) which, by radical co-polymerization with an appropriate monomer, leads to copolymers; other allyl linking arms are known [$-O(CH_2CH_2O)_2CH_2CH=CH_2$] (Fernández-Santana et al. 1989 Carbohydr Res 8: 531-537). Additionally, allyl linking arms can be derivatized in the presence of 2-aminoethanethiol to provide for a linking arm $-OCH_2CH_2CH_2SCH_2CH_2NH_2$ (Lee et al. 1974 Carbohydr Res 37: 193 et seq). Other suitable linking arms are disclosed in U.S. Pat. Nos. 4,137,401, 4,238,473, 4,362,720 and in Dahmen et al. (1984 Carbohyd Res 127: 15-25) and Garegg et al (1985 Carbohydr Res 136:207-213).

Additionally, as shown by Ratcliffe et al. (U.S. patent application Ser. No. 07/278,106), the R group can be an additional saccharide or an oligosaccharide containing a linking arm at the reducing sugar terminus.

Preferably, the a glycon moiety is a hydrophobic group and most preferably, the aglycon moiety is a hydrophobic group selected from the group consisting of $-(CH_2)_8COOCH_3$, $-(CH_2)_5OCH_2CH=CH_2$ and $-(CH_2)_8CH_2OH$.

The functional linking arm of the hyaluronic acid antigen is then used to attach the antigen to a biocompatible solid support. Such attachment is well known in the art and is disclosed, for example, by U.S. patent application Ser. No. 07/887,746.

Solid supports having combinations of two or more oligosaccharides comprising hyaluronic acid bound thereto may be used to remove anti-hyaluronic acid antibodies from the biofluid. Alternatively, the biofluid may be passed successively over a series of solid supports, each of which has one or more different hyaluronic acid antigens bound thereto, to remove anti-hyaluronic acid antibodies of different specificity.

In another aspect, the invention relates to an immunoabsorbent composition according to the invention for use in a method of attenuating antibody-mediated transplant rejection in a subject recipient of a transplant. In another aspect, the invention relates to method for attenuating antibody-mediated transplant rejection in a subject recipient of a transplant comprising
  (a) withdrawing antibody-containing body fluid from the recipient; and
  (b) removing preformed antibodies to hyaluroric acid from the withdrawn body fluid by extracorporeal perfusion of the body fluid over the immunoabsorbent composition to yield a perfused body fluid for reintroduction into the recipient.

In the context of the use of the immunosorbent composition of the invention, the fluid is any body fluid that comprises antibodies. In a more preferred embodiment, the body fluid is selected from blood (such as peripheral blood), serum or plasma. In a more preferred embodiment, the body fluid is blood. The blood is obtained from a subject recipient of a transplant by conventional techniques known by the skilled person. Anticoagulants including, but not limited to, heparin or citrate, are added to prevent coagulation. If desired, cells may be removed from the blood before it is subjected to anti-hyaluronic acid antibody depletion.

Withdrawal of body fluids from a subject can be performed by methods and devices known by the skilled in the art that comprise, but are not limited to, devices such as catheters, syringes, cannulae, or the apparatus draining fluid from a patient disclosed in U.S. Pat. No. 7,048,724; as well as methods such as thoracentesis (invasive procedure to remove fluid from the chest cavity), paracentesis (medical procedure for draining of fluid from a body cavity, usually the peritoneal cavity), pericardiocentesis (removing of fluid from the pericardium area) and dyalisis (hemodialysis, peritoneal dialysis, hemofiltration, intestinal dialysis). In a particular embodiment of the invention, the body fluid which is withdrawn from the body of the subject is blood. In a preferred embodiment of the invention, the blood is withdrawn from the body of the subject by hemoperfusion. The blood is withdrawn by conventional techniques and an anticoagulant (e.g., heparin, citrate) is typically added to it to prevent coagulation. If desired, cells may be removed from the blood before it is subjected to xenoantibody depletion.

Depletion of antibodies specific for the hyaluronic acid oligosaccharide is achieved by perfusing the blood over a solid support having one or more antigens bound to it. In the present invention, depletion of antibodies specific for the hyaluronic acid oligosaccharide is achieved by perfusing the blood over a solid support having hyaluronic acid antigens bound to it. Hyaluronic acid antigens comprise, but are not limited to, oligosaccharides comprising hyaluronic acid, in particular hyaluronic acid disaccharides, hyaluronic acid tetrasaccharides, hyaluronic acid hexasaccharides and/or hyaluronic acid decasaccharides.

The body fluid will be contacted with the solid support under conditions that promote binding between the antigens (hyaluronic acid oligosaccharides) bound to the support and complementary anti-hyaluronic acid antibodies present in said biofluid. A preferred apparatus and technique for carrying out extracorporeal hemoperfusion is described in U.S. patent application Ser. No. 07/270,950. Contact temperatures in the range of 35° C. to 40° C. are preferably used. The contact time will typically be in the range of 1 to 6 hours. The unbound portion of the biofluid (i.e., anti-hyaluronic acid antibodies-depleted blood or plasma or serum) is then collected for reintroduction into the patient or it can be reintroduced directly on a continuous basis. The removal of antibodies from the biofluid of the recipient can be carried out prior to transplantation or once the subject has been transplanted (it is typically repeated daily up to 8 times before transplantation) so that the graft is introduced in the substantial absence of the antibodies or at a time when the antibodies are present at relatively low titers. The recipient's antibody titer may be monitored by immunoassay. Insertion of the graft under such conditions lessens the likelihood of antibody-mediated hyperacute rejection (even though antibody titers may subsequently increase) and enhances graft survival. This phenomenon is variously termed "accommodation," "adaptation," or "anergy". Antibody removal may be continued after transplantation if necessary.

Conventional pharmacologic immunosuppression regimes employing nonspecific immunosuppressive agents such as those previously mentioned may be employed in conjunction.

In a particular embodiment, the preformed antibodies to hyaluronic acid are antibodies targeting oligosaccharides comprising hyaluronic acid. In a more particular embodiment, the preformed antibodies to hyaluronic acid oligosaccharides are antibodies targeting hyaluronic acid disaccharides, hyaluronic acid tetrasaccharides, hyaluronic acid hexasaccharides and/or hyaluronic acid decasaccharides.

In a particular embodiment, the transplant is a xenotransplant or an allotransplant.

In a particular embodiment, the transplant rejection is acute humoral rejection.

In a particular embodiment, the subject recipient of a transplant is a human or a non-human primate.

Polymeric Structures and Uses Thereof

In another embodiment, the invention relates to a polymeric structure comprising a polymeric backbone wherein one or more of the monomer units forming the polymeric backbone are linked to a hyaluronic acid oligosaccharide.

The polymer portion of the polymeric structure of this invention is comprised of at least two identical or different monomer units which are linked together in a linear or branched fashion, in the form of a ring (for example macrocycles), in the form of a star (dendrimers) or in the form of a ball (e.g., fullerenes), and may exhibit heterogeneity in molecular weight. Because the compounds of this invention are hydrophilic to at least some degree, the polymer portion should be hydrophilic to at least some degree. Skilled artisans readily will recognize a multitude of hydrophilic polymers which may be used with this invention. Where the polymeric structure according to this invention is to be used in vivo, it should be biodegradable, physiologically tolerated and physiologically degradable. In such cases, the polymer must meet a number of requirements in order to be physiologically tolerated. Namely, it must (i) induce no immune response in subjects in which it is to be used and (ii) avoid non-specific interactions and accumulation in the reticuloendothelial system (RES). Polymers suitable for in vivo use include polyamides, polycarbonates, polyiminocarbonates, polyanhydrides, polyorthoesters, polyesters, polydioxanones, polyhydroxycarboxylic acids, polyaminoacids (including poly-lysine), polyphosphazenes and polysaccharides. Preferred polymers include a polyamino-acid, a polyhydroxy-carboxylic acid linked as polyester, polyamide or anhydride, or a polysaccharide preferably having a molecular weight of up to about 70 kD. The polymer preferably has a molecular weight of at least about 2 kd in order to achieve a sufficient half-life in the blood.

Suitable polymers which are particularly preferred for in vivo use include polyaspartate-amides, polysuccinimides, polyglutamates and polylysine-fumaramides belonging to the polyamino-acids, the functional polyhydroxycarboxylic acids which belong to the polyhydroxycarboxylic acids and are based on malic acid, tartaric acid or citric acid in the form of their polyesters, polyamides or polyanhydrides, as well as substituted chitosans, heparins, hyaluronic acids or starch derivatives. Skilled artisans readily will recognize other suitable polymers.

The hyaluronic acid oligosaccharide forming part of the polymeric structures of the invention is selected from the group consisting of a hyaluronic acid disaccharide, a hyaluronic acid tetrasaccharides, a hyaluronic acid hexasaccharide a hyaluronic acid decasaccharides or a mixture of one or more of the above.

The degree of loading of the polymeric backbone with the carbohydrate portion (via spacer) is generally between about 0.5 and about 50 percent, preferably from about 2 to about 25 percent. The degree of loading varies depending on the desired function. The polymer may carry a plurality of hyaluronic acid oligosaccharides coupled via spacers or it may carry only a single, spacer-linked hyaluronic acid oligosaccharide. When there is a plurality of hyaluronic acid oligosaccharide, these may be identical or they may be different. The absolute number of hyaluronic acid oligosaccharides or spacer-hyaluronic acid oligosaccharides carried on the polymer also will vary depending on the particular hyaluronic acid oligosaccharide (disaccharide, tetrasaccharide, hexasaccharide or decasaccharides) and the intended use. Moreover, it may be advantageous, to link a plurality of the carbohydrate-containing polymers together.

The spacer is a moiety which connects, and provides spatial separation to the hyaluronic acid oligosaccharide portion and polymer portion. This spatial separation may be necessary to prevent steric interactions between hyaluronic acid oligosaccharide and the polymer, thereby ensuring optimal steric accessibility of the hyaluronic acid oligosaccharide portion. The spacer can be a naturally occurring molecule or a non-naturally occurring synthetic molecule.

To facilitate coupling of the spacer to the hyaluronic acid oligosaccharide and polymer portions, the spacer advantageously is bifunctional. A bifunctional spacer is a spacer which carries two reactive functional groups which may be used to link the spacer to an activated group in the polymer portion on the one hand and to another activated group on the hyaluronic acid oligosaccharide portion on the other hand, by formation of covalent bonds.

"Reactive groups" are functional groups which act as donor, preferably OH, $NH_2$ of SH functionalities, which react with "activated groups" to form a covalent bond. Particularly preferred in this regard are $NH_2$ or the OH group. Reactive groups actually are components of the polymer, as the polymer is composed of monomers which contain reactive groups.

"Activated groups" are functional groups which act as acceptor and react with the "reactive groups" to form a covalent bond. Preferably used are bromides, iodides, active esters, particularly preferably p-nitrophenyl or N-hydroxysuccinimide derivatives. Also preferred are carbonyl chlorides and imidazolides of carboxylic acids, mixed carboxylic anhydrides as well as phenyl radicals. Preferably used are aldehydes, acrylic esters, acrylamides, malonimide, succinimide, 2-vinylpyridine, iodoacetic esters, isothiocyanate and/or isocyanate. Most preferred are N-hydroxysuccinimide active radicals, maleimide, succinimide, acrylamides, aldehyde or isocyanate. Activated groups are either present as part of the polymer or can be prepared from reactive groups which are already part of the polymer by processes known to the skilled worker. R. C. Larock, COMPREHENSIVE ORGANIC TRANSFORMATIONS, VCK-Verlagsgesellschaft, Weinheim/Germany (1989).

The polymeric structures according to the invention can be used in attenuating antibody-mediated transplant rejection in a subject recipient of a transplant. Thus, in another aspect, the invention relates to the use of a polymeric structure according to the invention for use in a method of attenuating antibody-mediated transplant rejection in a subject recipient of a transplant. Alternatively, the invention is related to a method for attenuating antibody-mediated transplant rejection in a subject recipient of a transplant that comprises the administration of a polymeric structure of the invention in an amount sufficient to inhibit the antibodies of the recipient to said antigen.

The term "attenuating antibody-mediated transplant rejection" is referred to an amelioration or reduction of the transplant humoral rejection mediated by antibodies.

In a preferred embodiment, the polymeric structure is parenterally administered to the recipient in an amount sufficient to inhibit the antibodies of the recipient to said antigen.

The term "parenteral administration" is referred to the administration that comprises, but is not limited to, intravenous, intra-arterial, intra-muscular, intracerebral, intracerebroventricular and subcutaneous.

The term "preformed antibodies" relates to antibodies targeting oligosaccharides derived from hyaluronic acid that are present in a subject who has not been subjected to transplantation and/or prior to transplantation.

The parenteral administrable composition of the invention may be adapted as a sterile solution, a suspension or a lyophilized product in the appropriate unit dosage form. Adequate excipients can be used comprising, but not limited to:

antimicrobial preservatives, such as methylparaben, prophylparaben, etc.
    antioxidants, such as sodium metabisulfite, propyl gallate, etc
    stabilizing and suspending agents, such as soluble or swellable modified celluloses, e.g. carboxymethylcellulose sodium (Aquasorb, Blanose, Nymcel)
    tonicity agents, such as sodium chloride
    solubilizers, such as propyleneglycol or polyethyleneglycols The mentioned formulations will be prepared using standard methods such as those described or referred to in the Spanish and US Pharmacopoeias and similar reference texts.

The amount of polymeric structure to be administered is the amount necessary to inhibit the antibodies of the recipient to said antigen. Said amount is to be determined by the physician. In a particular embodiment, the antibodies of the recipient are antibodies targeting oligosaccharides comprising hyaluronic acid. In a more particular embodiment, the antibodies of the recipient are antibodies targeting hyaluronic acid disaccharides, hyaluronic acid tetrasaccharides, hyaluronic acid hexasaccharides and/or hyaluronic acid decasaccharides.

The composition can be accompanied as well of immunosupression agents.

In a particular embodiment, the transplant rejection is acute humoral rejection.

In another embodiment, the transplant is a xenotransplant or an allotransplant.

In another embodiment, the subject who has received a transplant is a human or a non-human primate.

Cells Stably Incorporating HA Oligosaccharides in their Surface and Uses Thereof In another embodiment, the invention relates to cells which stably incorporate HA oligosaccharides in their surface. These cells are obtained by insertion or incorporation into their cell membrane of exogenously prepared synthetic molecule constructs thereby effecting qualitative and quantitative changes in the cell surface antigens expressed by the cell.

Cells can be modified using any lipid anchor know in the art. In one embodiment, cells can be modified by a method which exploits the ability of GPI linked proteins to spontaneously anchor to the cell membrane via their lipid tails as described in WO9905255, which describes a method comprising the insertion of a GPI linked protein isolated from a biological source into a membrane. Isolated GPI-anchored proteins are stated as having an unusual capacity to reintegrate with a cell-surface membrane. Localising antigens to the cell surface may also be achieved by the use of glycolipids as membrane anchors. For instance, WO2003/034074 describes a method for decorating the surface of a cell with a molecule of interest which comprises the step of inserting a controlled amount of glycolipid into a membrane. The amount of glycolipid inserted is controlled to provide cells with a desired level of antigen expression. Moreover, WO2003087346 describes a method which includes the step of inserting a modified glycolipid into a membrane as a "membrane anchor". The modified glycolipid provides for the localisation of antigens to the surface of the cell or multicellular structure. New characteristics may thereby be imparted on the cell or multicellular structure.

In a preferred embodiment, the cells stably incorporating hyaluronic acid oligosaccharides are obtained by contacting a cell with a synthetic membrane anchor having the estructure F-S1-S2-L wherein F is a HA oligosaccharide, $S_1$-$S_2$ is a spacer linking F to L and L is a lipid which can be integrated into the lipid bilayer of the cell and which is selected from the group consisting of diacyl- and dialkyl-glycerolipids, including glycerophospholipids, and sphingosine derived diacyl- and dialkyl-lipids, including ceramide. Preferably L is a lipid selected from the group consisting of diacyl- and dialkyl-glycerolipids, including glycerophospholipids. More preferably L is selected from the group consisting of: diacylglycerolipids, phosphatidate, phosphatidyl choline, phosphatidyl ethanolamine, phosphatidyl serine, phosphatidyl inositol, phosphatidyl glycerol, and diphosphatidyl glycerol derived from one or more of trans-3-hexadecenoic acid, cis-5-hexadecenoic acid, cis-7-hexadecenoic acid, cis-9-hexadecenoic acid, cis-6-octadecenoic acid, cis-9-octadecenoic acid, trans-9-octadecenoic acid, trans-11-octadecenoic acid, cis-11-octadecenoic acid, cis-11-eicosenoic acid or cis-13-docsenoic acid. More preferably the lipid is derived from one or more cis-destaurated fatty acids. Most preferably L is selected from the group consisting of: 1,2-O-dioleoyl-sn-glycero-3-phosphatidylethanolamine (DOPE), 1,2-O-distearyl-sn-glycero-3-phosphatidylethanolamine (DSPE) and rac-1,2-dioleoylglycerol (DOG).

In a particular embodiment, the hyaluronic acid oligosaccharides are selected from the group consisting of hyaluronic acid disaccharides, hyaluronic acid tetrasaccharides, hyaluronic acid hexasaccharides and/or hyaluronic acid decasaccharides.

Cells which stably incorporate exogenous HA oligosaccharide on their surface are usually obtained by contacting a cell or multicellular structure with a glycolipid anchor. Preferably the concentration of the water soluble synthetic membrane anchor or synthetic molecule construct in the suspension is in the range 0.1 to 10 mg/mL. Preferably the temperature is in the range 2 to 37 degrees centigrade. More preferably the temperature is in the range 2 to 25 degrees centigrade. Most preferably the temperature is in the range 2 to 4 degrees centigrade In a preferred embodiment the cell is a red blood cell.

The cells stably incorporating exogenous HA oligosaccharides in their surface according to the invention can be used in attenuating antibody-mediated transplant rejection in a subject recipient of a transplant. Thus, in another aspect, the invention relates to a population of cells which stably incorporate HA oligosaccharides in their surface for use in a method of attenuating antibody-mediated transplant rejection in a subject recipient of a transplant. Alternatively, the invention is related to a method for attenuating antibody-mediated transplant rejection in a subject recipient of a transplant that comprises the administration of a population of cells which stably incorporate HA oligosaccharides in their surface in an amount sufficient to inhibit the antibodies of the recipient to said antigen.

The term "attenuating antibody-mediated transplant rejection" is referred to an amelioration or reduction of the transplant humoral rejection mediated by antibodies.

In a preferred embodiment, the cell population is parenterally administered to the recipient in an amount sufficient to inhibit the antibodies of the recipient to said antigen.

The term "parenteral administration" is referred to the administration that comprises, but is not limited to, intravenous, intra-arterial, intra-muscular, intracerebral, intracerebroventricular and subcutaneous.

The term "preformed antibodies" relates to antibodies targeting oligosaccharides derived from hyaluronic acid that are present in a subject who has not been subjected to transplantation and/or prior to transplantation.

The parenteral administrable composition of the invention may be adapted as a sterile solution, a suspension or a lyophilized product in the appropriate unit dosage form. Adequate excipients can be used comprising, but not limited to:

- antimicrobial preservatives, such as methylparaben, prophylparaben, etc.
- antioxidants, such as sodium metabisulfite, propyl gallate, etc stabilizing and suspending agents, such as soluble or swellable modified celluloses, e.g. carboxymethylcellulose sodium (Aquasorb, Blanose, Nymcel)

tonicity agents, such as sodium chloride solubilizers, such as propyleneglycol or polyethyleneglycols The mentioned formulations will be prepared using standard methods such as those described or referred to in the Spanish and US Pharmacopoeias and similar reference texts.

The amount of cell population to be administered is the amount necessary to inhibit the antibodies of the recipient to said antigen. Said amount is to be determined by the physician. In a particular embodiment, the antibodies of the recipient are antibodies targeting oligosaccharides comprising hyaluronic acid. In a more particular embodiment, the antibodies of the recipient are antibodies targeting hyaluronic acid disaccharides, hyaluronic acid tetrasaccharides, hyaluronic acid hexasaccharides, and/or hyaluronic acid decasaccharides.

The composition can be accompanied as well of immunosupression agents.

In a particular embodiment, the transplant rejection is acute humoral rejection.

In another embodiment, the transplant is a xenotransplant or an allotransplant.

In another embodiment, the subject who has received a transplant is a human or a non-human primate.

Uses of Antigens of the Invention/Methods for Attenuating Transplant Rejection

The invention also contemplates parenterally introducing hyaluronic acid antigen into the transplant recipient. Once introduced into the circulation, these antigens will bind to pre-formed antibodies specific for at least one hyaluronic acid oligosaccharide and will neutralize the activity of said antibodies.

Thus, in another aspect, the present invention is related to a hyaluronic acid oligosaccharide for use in attenuating antibody-mediated transplant rejection in a subject recipient of a transplant. Alternatively, the invention is related to a method for attenuating antibody-mediated transplant rejection in a subject recipient of a transplant that comprises the administration of hyaluronic acid oligosaccharide in an amount sufficient to inhibit the antibodies of the recipient to said antigen.

The term "attenuating antibody-mediated transplant rejection" is referred to an amelioration or reduction of the transplant humoral rejection mediated by antibodies.

In a preferred embodiment, the hyaluronic acid oligosaccharide is parenterally administered to the recipient in an amount sufficient to inhibit the antibodies of the recipient to said antigen.

The term "parenteral administration" is referred to the administration that comprises, but is not limited to, intravenous, intra-arterial, intra-muscular, intracerebral, intracerebroventricular and subcutaneous.

The term "preformed antibodies" relates to antibodies targeting oligosaccharides derived from hyaluronic acid that are present in a subject who has not been subjected to transplantation and/or prior to transplantation.

The parenteral administrable composition of the invention may be adapted as a sterile solution, a suspension or a lyophilized product in the appropriate unit dosage form. Adequate excipients can be used comprising, but not limited to:

antimicrobial preservatives, such as methylparaben, prophylparaben, etc.

antioxidants, such as sodium metabisulfite, propyl gallate, etc stabilizing and suspending agents, such as soluble or swellable modified celluloses, e.g. carboxymethylcellulose sodium (Aquasorb, Blanose, Nymcel)

tonicity agents, such as sodium chloride solubilizers, such as propyleneglycol or polyethyleneglycols The mentioned formulations will be prepared using standard methods such as those described or referred to in the Spanish and US Pharmacopoeias and similar reference texts.

The amount of hyaluronic acid antigen to be administered is the amount necessary to inhibit the antibodies of the recipient to said antigen. Said amount is to be determined by the physician. In a particular embodiment, the antibodies of the recipient are antibodies targeting oligosaccharides comprising hyaluronic acid. In a more particular embodiment, the antibodies of the recipient are antibodies targeting hyaluronic acid disaccharides, hyaluronic acid tetrasaccharides, hyaluronic acid hexasaccharides and/or, hyaluronic acid decasaccharides.

The same hyaluronic acid antigens that are used in the anti-hyaluronic acid antibody removal technique may be used in the inhibition technique. One or more of these hyaluronic acid antigens or pharmaceutically acceptable derivatives thereof (e.g., esters) is formulated as an injectable in a conventional pharmaceutically acceptable injectable vehicle (e.g., water for injection). Formulation typically involves mixing the antigen(s) with the vehicle, depyrogenating the mix by ultrafiltration and sterile filtering the depyrogenated mix. The mix may be lyophilized for storage and reconstituted in sterile vehicle if desired. The injectable formulation may be administered by intermittent bolus injection or by continuous intravenous infusion. The administration will typically be initiated before revascularization of the transplant and continued for a varying period of time following transplantation. The particular dosing and administration regimen may vary depending upon the type of transplant, the age, weight, and medical history of the recipient and donor, and the pharmacokinetics of the antigen(s). Typically, the antigens will be administered continuously at doses ranging between about 100 mg/hr and 1000 mg/hr for 1 to 20 days. Concomitant pharmacologic immunosuppression is preferred. Extracorporeal removal of antibodies as described previously may be used in combination with parenteral administration of antigens.

The composition can be accompanied as well of immunosupression agents.

In a particular embodiment, the transplant rejection is acute humoral rejection.

In another embodiment, the transplant is a xenotransplant or an allotransplant.

In another embodiment, the subject who has received a transplant is a human or a non-human primate.

Blood, Plasma or Serum Depleted of Antibodies Specific for Hyaluronic Acid Oligosaccharides In another aspect, the invention is related to blood or plasma or serum useful for infusing into a subject recipient of a transplant to attenuate transplant rejection, the blood or plasma being depleted of preformed antibodies to hyaluronic acid.

This blood, plasma or serum can be obtained by means of the immunoabsorbent composition of the invention, as previously described.

Preformed antibodies are antibodies targeting oligosaccharides comprising hyaluronic acid. In particular, preformed antibodies are antibodies targeting hyaluronic acid disaccharides, hyaluronic acid tetrasaccharides, hyaluronic acid hexasaccharides and/or hyaluronic acid decasaccharides.

In a preferred embodiment, the transplant rejection is acute humoral rejection. In another preferred embodiment, the transplant is a xenotransplant or an allotransplant. In yet another preferred embodiment, the subject recipient of a transplant is a human or a non-human primate.

Method for Diagnosing SLE in a Subject

The authors of the present invention have observed that systemic lupus erythematosus (SLE) patients show reduced IgM and augmented IgG anti-HA disaccharide antibodies, suggesting that changes in anti-HA antibodies may be related to the immunogenicity of particular HA oligosaccharides, not the whole HA molecule.

Thus, in another aspect, the present invention relates to a method for diagnosing systemic lupus erythematosus (SLE) in a subject comprising determining in a sample from said subject the levels of antibodies specific for at least one hyaluronic acid oligosaccharide, wherein if the levels of antibodies specific for said at least one hyaluronic acid oligosaccharide are modified with respect to a reference value, then the subject is diagnosed with SLE.

In a first aspect, the SLE diagnostic method of the invention comprises the determination of the levels of antibodies specific for at least a hyaluronic acid oligosaccharide in a sample from a subject. Suitable methods for determining the levels of antibodies specific for at least a hyaluronic acid oligosaccharide have been described above in the context of the method for determining the probability of transplant rejection in a subject. In a preferred embodiment of the invention, the levels of antibodies specific for at least one hyaluronic acid oligosaccharide are determined in a sample from a subject by means of ELISA or immunohistochemistry.

In a particular embodiment, the antibodies specific for at least one hyaluronic acid oligosaccharide which are determined according to the diagnostic method of the invention are selected from the group consisting of one or more of IgA, IgD, IgE, IgG, and IgM. In a preferred embodiment, the antibodies specific for at least one hyaluronic acid oligosaccharide are determined from the group consisting of one or more of IgG or IgM. In a preferred embodiment, the antibodies which are determined in the method according to the present invention are selected from the group consisting of IgM antibodies against HA disaccharide, IgM antibodies against the HA tetrasaccharide, IgM antibodies against the HA hexasaccharides IgM antibodies against the HA decasaccharides, IgG antibodies against HA disaccharide, IgG antibodies against the HA tetrasaccharides, IgG antibodies against the HA hexasaccharides and/or IgG antibodies against the HA decasaccharides.

In a second step, the SLE diagnostic method of the invention comprises comparing the level of antibodies specific for at least one hyaluronic acid oligosaccharide as determined in the first step to a reference value, wherein if the levels of antibodies specific for at least one hyaluronic acid oligosaccharide in said sample are modified when compared to a reference value, then the subject is diagnosed with SLE.

The term "modified" or "substantially modified" has been previously described in the context of the method for determining the probability of transplant rejection in a subject.

In the context of the SLE diagnostic method of the invention, the term "reference value" relates to the level of antibodies specific for at least one hyaluronic acid oligosaccharide in a sample from a healthy subject or from a subject who has not been diagnosed with SLE.

Once this reference value is established, the level of antibodies specific for at least one hyaluronic acid oligosaccharide in a subject to be diagnosed can be compared with this reference value, and thus be assigned a "low" or "decreased" level of antibodies specific for at least one hyaluronic acid oligosaccharide if it is under this reference value, or a level of "high" or "increased" level of antibodies specific for at least one hyaluronic acid oligosaccharide if it is above this reference value.

In particular, an "increase" of the level of antibodies specific for at least one hyaluronic acid oligosaccharide when compared to the reference value of at least 1.1-fold, 1.5-fold, 5-fold, 10-fold, 20-fold, 30-fold, 40-fold, 50-fold, 60-fold, 70-fold, 80-fold, 90-fold, 100-fold or even more compared with the reference value is considered as "increased" levels of anti-hyaluronic acid antibody. A "decrease" of the level of antibodies specific for at least one hyaluronic acid oligosaccharide when compared to the reference value of at least 0.9-fold, 0.75-fold, 0.2-fold, 0.1-fold, 0.05-fold, 0.025-fold, 0.02-fold, 0.01-fold, 0.005-fold or even less compared with reference value is considered as "decreased" levels of antibodies specific for at least one hyaluronic acid oligosaccharide.

Once a comparison between the levels of antibodies specific for at least one hyaluronic acid oligosaccharide in a sample from a subject to be diagnosed with SLE and the reference value has been made, the diagnostic method of the invention allows determining the diagnosis, wherein if the levels of antibodies specific for at least one hyaluronic acid oligosaccharide are modified when compared to a reference value, then the subject is diagnosed with SLE.

In a particular embodiment, the antibodies specific for at least one hyaluronic acid oligosaccharide are determined from the group consisting of one or more of IgG or IgM.

In a particular embodiment, the level of IgM antibodies specific for at least one hyaluronic acid oligosaccharide are determined in a sample from a subject to be diagnosed with SLE, wherein if the levels of IgM antibodies specific for said at least one hyaluronic acid oligosaccharide are decreased with respect to a reference value, then the subject is diagnosed with SLE.

In another particular embodiment, the level of IgG antibodies specific for at least one hyaluronic acid oligosaccharide are determined in a sample from a subject to be diagnosed with SLE, wherein if the levels of IgG antibodies specific for said at least one hyaluronic acid oligosaccharide are increased with respect to a reference value, then the subject is diagnosed with SLE.

In a particular embodiment, the antibodies specific for at least one hyaluronic acid oligosaccharide are antibodies targeting hyaluronic acid disaccharides, hyaluronic acid tetrasaccharides, hyaluronic acid hexasaccharides and/or hyaluronic acid decasaccharides.

In a particular embodiment, the sample is selected from the group consisting of blood, serum and plasma. In a preferred embodiment, the sample is a blood sample.

In a particular embodiment, the subject to be diagnosed with SLE is a mammal. In a preferred embodiment, the subject is a human.

The invention is described in detail below by means of the following examples which are to be construed as merely illustrative and not limitative of the scope of the invention.

EXAMPLES

Animals, Materials and Methods

Animals. The in-life studies were performed at the Juan Canalejo Medical Center. A total of 9 baboons (*Papio anubis*) (Consort Bioservices, Steyming, United Kingdom), were included in this studies. Five animals received a pig organ xenotransplant (4 hearts and one kidney) whilst the other 4 were exposed to pig red blood cells (PRBC). Pigs transgenic for human complement regulatory protein DAF (hDAF) (provided by Imutran, Cambridge, United Kingdom) and non-transgenic, weighting 10-20 kg, were housed in a facility approved and accredited by the Galicia Department of Agriculture. The studies were approved and monitored by the Research Committee of Juan Canalejo Medical Center.

Transplant Procedures and Blood Samples for Anti-Carbohydrate Antibody Analysis.

Heterotopic pig heart and kidney were placed in the abdominal cavity of baboons as previously described (Schmoeckel M et al. 1998 Transplantation 65:1570-1577; Cozzi E et al. 1997 Transplantation. 64:1383-1392). Blood samples for anti-carbohydrate antibody analysis were obtained from each animal before transplantation and at acute humoral xenotransplant rejection (AHXR).

PRBC Immunization and Blood Samples for Anti-Carbohydrate Antibody Analysis.

Three animals (D29, E19 and E7) were exposed to weekly injections of 5 cubic centimeters (cc) of PRBC three times and blood samples for anti-carbohydrate antibodies were analysed one week after last injection. Another animal received 7 daily injections of 5 cc of PRBC (C63), until an augment of the level of anti-pig hemolytic antibodies (APHA) was observed, and blood samples were analysed at days 2, 20 and 30 relative to the first PRBC injection.

GAS914 Treatment.

Four of the five transplant recipients received GAS 914 (Novartis Pharma A.G., Basel, Switzerland) to deplete anti-αGal antibodies (4). The dose was 5 mg/kg/d on days −17, −14, and −11; 1 mg/kg/d from day −5 to 0; and 1 mg/kg/12 h after transplantation until rejection. All the animals but one (E19) exposed to PRBC were treated with 1 mg/kg/day of GAS914 subcutaneously from day −5 relative to the first PRBC injection to 10 days after the last injection. Thereafter, they were treated with 1 mg/kg of GAS914 every other day until day 30 of the first PRBC injection.

Immunosuppression:

Immunosuppression in transplant experiments consisted of cyclophosphamide (CyP) for induction only, cyclosporine (CyA), mycophenolate sodium (MPS, Novartis Pharma A.G., Basel, Switzerland) and steroids. CyP at 40 mg/kg was administered intravenously on day −1, and at 20 mg/kg on days 0, 2 and 4, with the last dose adjusted according to total white blood cell count (lower limit $2 \times 10^9$/L). CyA was started orally on day −1 at a dose of 100 mg/kg/12 hours. After transplantation CyA dose was adjusted to maintain a blood trough level between 1,000 and 1,500 ng/ml, which is the adequate target in baboons. MPS was initiated orally on day −1 at a dose of 35 mg/kg/12 hours. After transplantation MPS dose was adjusted to maintain blood mycophenolic acid trough levels between 4 and 6 µg/ml and according of the clinical condition of the recipient. Methylprednisolone was given at 1 mg/kg intravenously on days 0, 1 and 2, and reduced by 0.05 mg/kg/day to reach a maintenance dose of 0.2 mg/kg. Biopsy-proven rejection of the pig heart or increases in APHA above 15% were treated with three pulses of 15 mg/kg methylprednisolone once daily for three days.

One baboon exposed to PRBC (C63) was treated on day 20 with 200 mg/kg of cyclophosphamide (CyP) over 4 days. The dose of CyP was chosen because it largely eliminates the mature immune system, leading to a major reduction in antibody and autoantibody levels, while leaving hematopoietic precursors intact. Unfortunately, the animal died on day 31 because of side effects from CyP treatment.

Histopathological Studies.

In all the transplants an open xenograft biopsy was obtained 30 minutes after reperfusion, as well as at autopsy after AHXR. Tissue samples were fixed in 10% buffered formalin for at least 24 hours, dehydrated, and embedded in paraffin. Sections of 4 µm thickness were stained with hematoxylin and eosin Immunohistochemical examinations for IgG and IgM were performed in paraffin-embedded material. After inhibition of endogenous alkaline phosphatase with levamisol for 10 minutes, samples were incubated with goat anti-human IgG and IgM alkaline phosphatase conjugated (Sigma-Aldrich) for 30 minutes at 1:50 dilution. Tissue samples where then incubated with the EnVision™ G|2, Rabbit/Mouse (LINK) (Dako) following product recommendations. This reagent is a dextran polymer, which also carries antibodies to rabbit and mouse immunoglobulins. Finally, an alkaline phosphatase-labelled amplification polymer is added. The reaction is visualized by Permanent Red Chromogen also included in the kit. To investigate the potential role of hyaluronan as antigen some tissue sections were pre-treated with 50 u/mL of *Streptomyces* hyaluronidase (Sigma-Aldrich) for two hours at 37° C., which unlike other hyaluronidases is specific for hyaluronan.

Glycan Array Screening.

The carbohydrate-binding specificity of baboon serums obtained before and after pig organ xenotransplantation or PRBC exposure was investigated on glycan array v4.1 comprised of 406 glycans (Consortium for Functional Glycomics, Protein-Glycan Interaction Core-H) (http://www.functionalglycomics.org). Two different studies were performed: Consortium for Functional Glycomics projects #1313 and #1577. Pre and post-immunization samples from each animal were analysed in the same glycoarray study with exception of C63 day 20, which was performed in study #1577 whilst the other samples from this animal were analysed in study #1313. In order to assess the potential effect of a different glycoarray study, a linear mixed model with repeated measures was fitted for each carbohydrate, with its log expression as dependent variable and type of sample (pre or post-immunization) and the study (#1313 or #1577) as independent variables.

Generation of Anti-Carbohydrate Antibodies in Rats.

Rats were immunized either with PRBC and hamster blood following two protocols to produce mainly IgM or IgG anti-carbohydrate antibodies. Three injections of 1 ml every other day (days 0, 2 and 4) and drawn of blood sample on day 5 was used to investigate IgM antibodies, and three injections every two weeks times 3, with blood obtained 12 days after last injection was used to investigate IgG antibodies.

Specific ELISA for HA Oligosaccharides.

The enzyme-linked immunosorbent assay (ELISA) plates were coated with HA oligosaccharides (disaccharide, tetrasaccharide and decasaccharide) conjugated with polyacrylamide, obtained from Shemyakin-Ovchinnikov Institute of Biorganic Chemistry, Russian Academy of Science (Moscow, Russia). The disaccharide form was synthesized in this institution, whilst the tetrasaccharide and decasaccharide molecules were obtained from Sigma, Spain, and bound to polyacrylamide in this center. The protocol for determination of anti-HA antibodies was based in previously described ELISAs to determine other anti-carbohydrate antibodies with minimal modifications (Mañez R et al. 2001 Xenotransplantation 8: 15-23; Obukhova P et al. 2007 Xenotransplantation 14: 627-635).

Results

Pig-to-Baboon Organ Xenotransplantation

The 4 hearts xenotransplantations into baboons were performed with organs from pigs transgenic for the human complement regulatory protein DAF (hDAF), whilst the kidney xenotransplantation was from a non-transgenic (wild) animal (Table 1). Anti-αGal antibodies were depleted before and after transplantation in three baboons (two hearts and the kidney recipient) and all the animals but one received a multiagent immunosuppression regimen that included CyP for induction and maintenance with MPA, CyA and steroids. All the animals were euthanized after AHXR, which occurred between 4 days and 60 days after transplantation, and was severe in four cases (Grade III) and mild in one case (Grade I) (Table 1).

Figure 2:
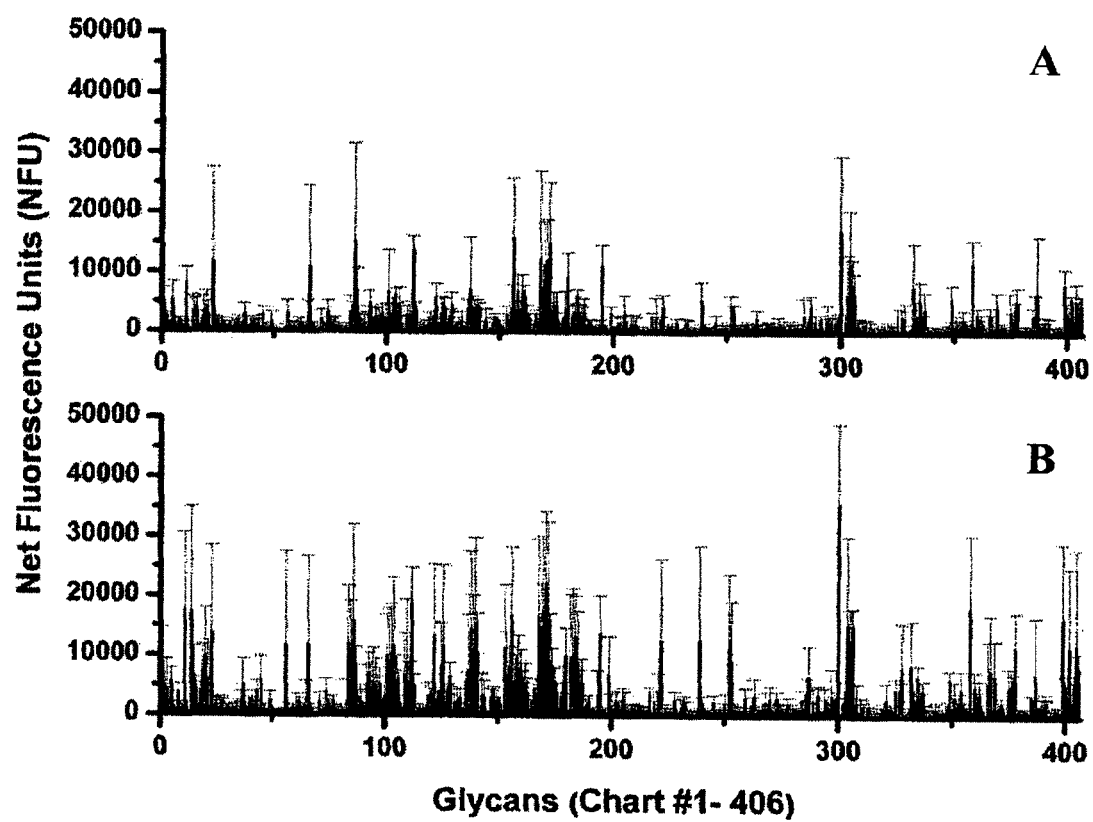
FIG. 2 shows the levels of anti-carbohydrate antibodies bound to glycan array in non-human primates before pig red blood cells (PRBC) exposure (A) and one week or 13 days after PRBC exposure (B). Results represent the mean and standard deviation (S.D.) of the four experiments.

Anti-Carbohydrate Antibodies in Non-Human Primates Before Pig Organ Xenotransplantation or PRBC Exposure The specificities of anti-carbohydrate antibodies in healthy baboons before receiving a pig organ or being exposed to PRBC are shown in FIGS. 1A and 2A, respectively. The pattern was very similar in both groups of animals with 15 of the top 20 average reactivities identical in both groups. The average level of antibodies against hyaluronan disaccharide (#300; GlcAβ1-3GlcNAcβ) showed the highest reactivity in baboons before exposure to PRBC and the second highest reactivity in those animals that underwent a pig organ xenotransplantation. This was valid even for those animals in which antibodies against Gal (#104) were not removed (A15, A14) or a blood sample was available before giving GAS914 (C63), with an average±S.D. of 18332±14201 net fluorescence units (NFU) for anti-hyaluronan disaccharide antibodies and 3865±2892 for anti-Gal antibodies.

Anti-Carbohydrate Antibodies in Non-Human Primates after Pig Organs Xenotransplantation or PRBC Exposure The average binding of antibodies increased at least 1000 NFU to 49 carbohydrates after pig organ xenotransplanta-

TABLE 1

Type of pig, organ, immunosuppresion protocol, survival and terminal xenograft histology for the individual non-human primates included in the study

| Animal ID | Pig | Organ | GAS914 | Immunosuppresion | Survival (days) | Xenograft histology |
|---|---|---|---|---|---|---|
| A15 | hDAF | Heart | No | No | 4 | AHXRIII |
| A14 | hDAF | Heart | No | CyP; MPS, CyA, Steroids | 24 | AHXRIII |
| D10 | hDAF | Heart | Yes | CyP; MPS, CyA, Steroids | 60 | AHXRI |
| D12 | hDAF | Heart | Yes | CyP; MPS; CyA, Steroids | 7 | AHXRIII |
| D17 | No hDAF | Kidney | Yes | CyP; MPS; CyA, Steroids | 12 | AHXRIII |

PRBC Immunization

Pig blood injections were not associated with side effects in any animal Only one animal died (C63) on day 30 after the initial PRBC injection as result of the side effects of the CyP treatment that received on day 20.

tion and 144 after PRBC exposure compared to baseline samples (FIGS. 1B and 2B). Antibodies against hyaluronan disaccharide (HAd) were the only present within the 20 higher increases both after pig organ xenotransplantation and PRBC exposure (Tables 2 and 3).

TABLE 2

Top 20 post-xenotransplantation increments in average compared to baseline samples

| Glycan number | Name | Increment (NFU) |
|---|---|---|
| 369 | Galα1-3(Fucα1-2)Galβ1-3GlcNAcβ1-2Manα1-3(Galα1-3(Fucα1-2)Galβ1-3GlcNAcβ1-2Manα1-6)Manβ1-4GlcNAcβ1-4GlcNAcβ-Sp20 | 6629 |
| 366 | Galα1-3(Fucα1-2)Galβ1-4GlcNAcβ1-2Manα1-3(Galα1-3(Fucα1-2)Galβ1-4GlcNAcβ1-2Manα1-6)Manβ1-4GlcNAcβ1-4GlcNAcβ-Sp20 | 5735 |
| 95 | Galα1-3(Fucα1-2)Galβ1-4(Fucα1-3)GlcNAcβ-Sp0 | 5487 |
| 160 | GlcNAcβ1-3GalNAcα-Sp8 α β | 5481 |
| 287 | Galα1-3(Fucα1-2)Galβ-Sp18 | 5425 |
| 87 | GalNAcβ1-3GalNAcα-Sp8 | 4965 |
| 300 | GlcAβ1-3GlcNAcβ-Sp8 | 4272 |
| 161 | GlcNAcβ1-3Galβ-Sp8 | 4074 |
| 401 | Galα1-4Galβ1-4GlcNAcβ1-2Manα1-3(Galα1-4Galβ1-4GlcNacβ1-2Manα1-6)Manβ1-4GlcNacβ1-4GlcNacβ-L VaNKT | 4073 |
| 158 | GlcNAcβ1-3(GlcNAcβ1-6)GalNAcα-Sp8 | 3844 |
| 97 | Galα1-3(Fucα1-2)Galβ1-4Glcβ-Sp0 | 3795 |

TABLE 2-continued

Top 20 post-xenotransplantation increments in average compared to baseline samples

| Glycan number | Name | Increment (NFU) |
|---|---|---|
| 96 | Galα1-3(Fucα1-2)Galβ1-4GlcNAc-Sp0 | 3746 |
| 156 | GlcNAcα1-6Galβ1-4GlcNAcβ-Sp8 | 3715 |
| 377 | GlcNAcβ1-3GalNAcα-Sp14 | 3458 |
| 166 | GlcNAcβ1-3Galβ1-4Glcb-Sp0 | 3266 |
| 404 | Galβ1-3GlcNAcα1-6Galβ1-4GlcNAcβ-Sp0 | 3182 |
| 327 | Galα1-4Galβ1-4GlcNAcβ1-3Galβ1-4Glcβ-Sp0 | 2758 |
| 406 | GlcNAcβ1-6(GlcNAcβ1-3)GalNAcα-Sp14 | 2740 |
| 358 | Galα1-3Galβ1-4GlcNAcβ1-2Manα1-3(Galα1-3Galβ1-4GlcNAcβ1-2Manα1-6)Manβ1-4GlcNAcβ1-4GlcNAcβ-Sp20 | 2647 |
| 98 | Galα1-3(Fucα1-2)Galβ-Sp8 | 2622 |

TABLE 3

Top 20 post-PRBC exposure increments in average compared to baseline samples

| Glycan Number | Name | Increment (NFU) |
|---|---|---|
| 300 | GlcAβ1-3GlcNAcβ-Sp8 | 18550 |
| 14 | Neu5Acβ-Sp8 | 13790 |
| 140 | Galβ1-4GalNAcα1-3(Fucα1-2)Galβ1-4GlcNAcβ-Sp8 | 11096 |
| 138 | Galβ1-4[6OSO3]Glcβ-Sp0 | 10507 |
| 11 | Rha-Sp8 | 9468 |
| 171 | (GlcNAcβ1-4)5β-Sp8 | 9419 |
| 405 | GalNAcβ1-3Galα1-6Galβ1-4Glcβ-Sp8 | 8849 |
| 84 | GalNAcα1-3GalNAcβ-Sp8 | 8766 |
| 56 | Fucα1-2Galβ1-3GalNAcβ1-3Galα1-4Galβ1-4Glcβ-Sp9 | 8602 |
| 306 | HOOC(CH3)CH-3-O-GlcNAcβ1-4GlcNAcβ-Sp10 | 8513 |
| 222 | Neu5Acα2-3Galβ1-3GalNAcβ1-3Galα1-4Galβ1-4Glcβ-Sp0 | 8490 |
| 153 | Galβ1-4Glcβ-Sp0 | 8207 |
| 399 | GalNAcα1-3GalNacβ1-3Galα1-4Galβ1-4GlcNacβ-Sp0 | 8197 |
| 126 | Galβ1-3GalNAcβ1-3Galα1-4Galβ1-4Glcβ-Sp0 | 7908 |
| 252 | Neu5Acβ2-6GalNAcα-Sp8 | 7828 |
| 122 | Galβ1-3(Neu5Acβ2-6)GalNAcα-Sp8 | 7721 |
| 169 | GlcNAcβ1-4Galβ1-4GlcNAcβ-Sp8 | 7611 |
| 139 | Galβ1-4[6OSO3]Glcβ-Sp8 | 7576 |
| 239 | Neu5Acα2-3Galβ1-4Glcβ-Sp8 | 7281 |
| 184 | GlcAβ1-3Galβ-Sp8 | 7087 |

Figure 3:
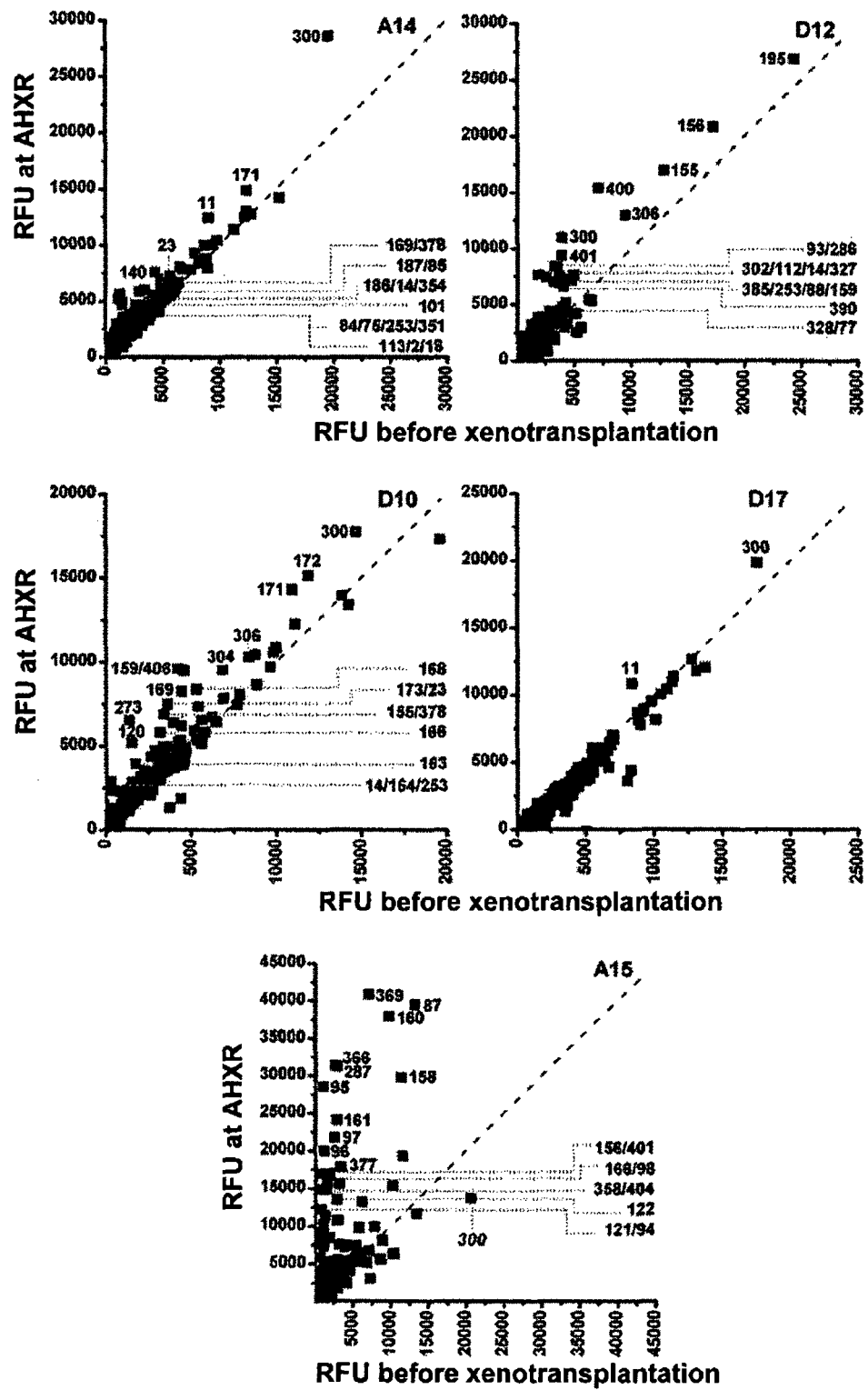
FIG. 3 shows a glycoarray analysis of individual sera from non-human primates before pig organ xenotransplantation and at AHXR.

The reactivity of anti-carbohydrate antibodies after pig organ xenotransplantation compared to before transplantation for each non-human primate is shown in FIG. 3. Antibodies against HA disaccharide were the only ones present in 4 out 5 of the top 20 augments of anti-carbohydrate antibodies at AHXR (FIG. 3). There were two cases with a moderated augment of anti-HA disaccharide antibodies. One was the case of mild rejection (D10) and the other was the kidney xenotransplantation (D17), in which these antibodies and those against L-Rhamnose (#11) were the only anti-carbohydrate antibodies that augmented at AHXR, whilst all the other barely changed. More significant raises of anti-HA disaccharide were observed in other two cases of severe rejection (A14 and D12). The exception was case A15 that was the only case in which the augment of reactivity of anti-HA disaccharide was not among the 20 largest increases. On the contrary, it was one of the 35 carbohydrates with a decreased reactivity after xenotransplantation compared to before transplantation, and showed the highest drop. The xenotransplantation in this case had the shortest survival (4 days) because no treatment was used. This suggests that, similarly to what happens with other performed antibodies such as anti-aGal, the excess of antigen after transplantation is associated with an initial decrease of antibodies until production of new antibodies generates an excess of antibodies. However, the production anti-HA disaccharide appears to be delayed compared to anti-aGal antibodies that occurs within two or three days after xenotransplantation.

Figure 4:
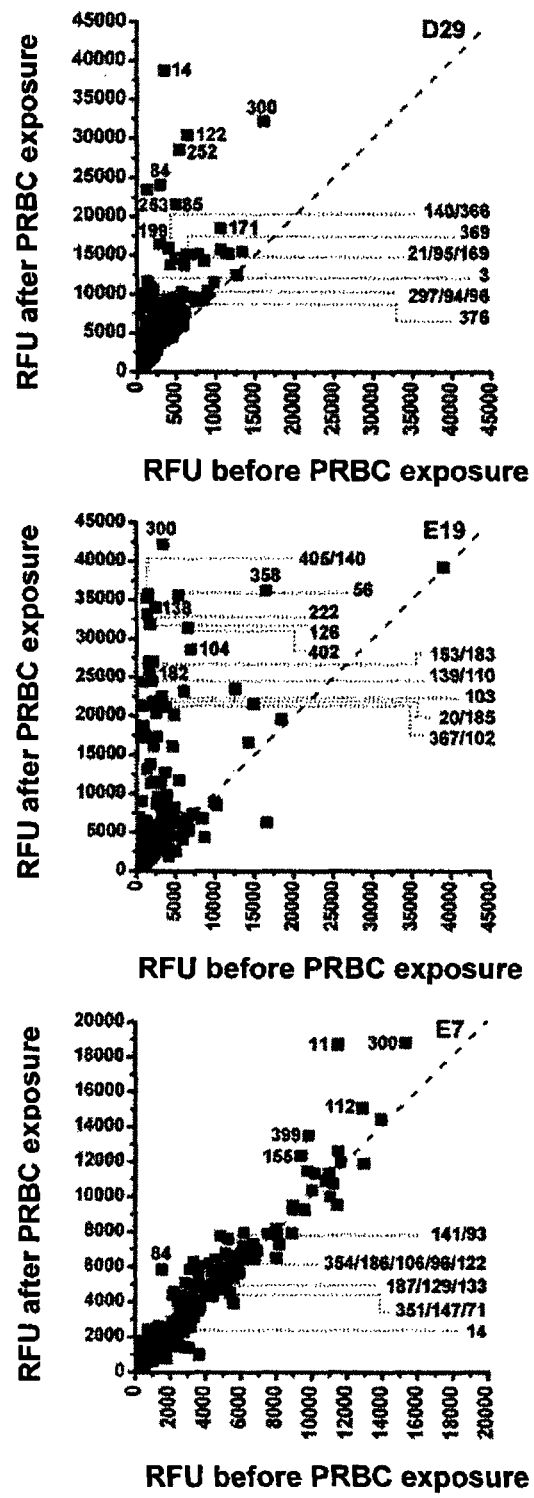
FIG. 4 shows a glycoarray analysis of individual sera from non-human primates before PRBC exposure and at different times points after PRBC exposure (D29, E19 and E7 one week after last PRBC exposure; C63 on day 2 of PRBC exposure and 13 or 23 days after last PRBC exposure).
Figure 4:
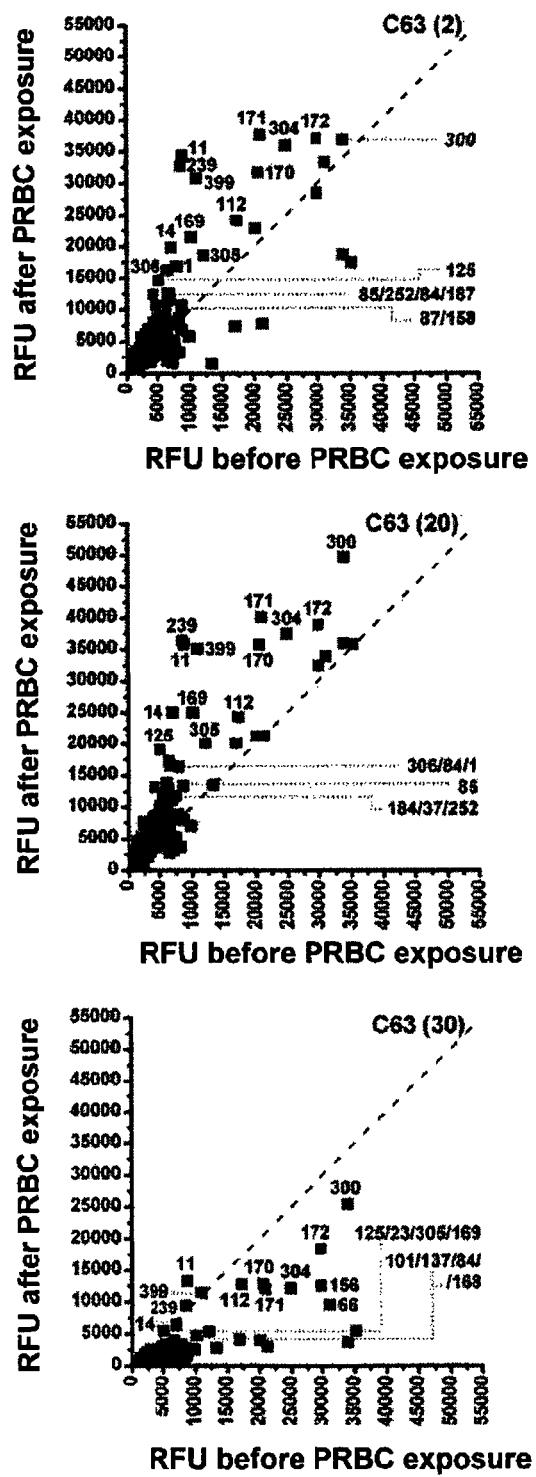

Anti-HA disaccharide antibodies were the only ones present in the top 20 increases after PRBC exposure in all the cases (FIG. 4). Antibodies against neuraminic acid (#14) were among the 20 highest augments in 3 out 4 cases, but barely changed in E19 where anti-HA disaccharide showed the higher level and increase after PRBC exposure. Interestingly, the augment of anti-HA disaccharide antibodies was not present on day two, during PRBC exposure, in animal C63, though it was evidenced on day 20, two weeks after the end of PRBC injections. This would support the delayed augment of anti-HA disaccharide antibodies compared to many other anti-carbohydrate antibodies as occurred on day two in C63 (FIG. 4). Once the increase of anti-HA disaccharide occurs remain for longer periods of time. In animal C63 most of anti-carbohydrate antibodies decreased on day 30 after CyP treatment (FIG. 4), but even in this situation anti-HA disaccharide showed the higher level of anti-carbohydrate antibodies.

Impact of Hyaluronidase on IgG and IgM Antibody Deposits in Xenografts at AHXR

To investigate the potential impact of HA antigens in AHXR, the presence of IgM and IgG deposits in tissue samples was investigated with and without previous incubation with *Streptomyces* hyaluronidase, which is specific for HA. Table 4 shows a semiquantitative score for grading antibody deposits.

TABLE 4

IgM and IgG antibody deposits in xenografts at AHXR with/without hyaluronidase treatment

| | | Without Hyaluronidase | | With Hyaluronidase | |
|---|---|---|---|---|---|
| Animal ID | AHXR | IgM | IgG | IgM | IgG |
| A15 | III | +++ | +++ | +++ | − |
| A14 | III | +++ | +++ | + | − |
| D10 | I | + | +++ | − | − |
| D12 | III | +++ | +++ | + | + |
| D17 | III | +++ | +++ | +++ | + |

All cases with severe AHXR showed significant deposits of IgM, which were minimal in the mild AHXR (D10), whilst notable deposits of IgG were present in all the cases. Pre-treatment of tissue samples with hyaluronidase was associated with the complete disappearance of IgG deposits in three cases (A15, A14 and D10), and with a remarkable reduction in the other two (D12 and D17). IgM deposits disappeared in one case (D10), were notably reduced in two (A14 and D12), and did not show any change in other two (A15 and D17). This indicates that HA antigens are present on endothelial cells at AHXR. The IgG deposits present in xenografts at AHXR target mainly HA antigens, whilst IgM may target these but also other antigens. In the case of A15 αGal is the most likely antigen for IgM antibodies, whereas in D17 is unclear.

The expression of HA on cultured endothelial cell lines and primary endothelial cultures is inducible by the proinflammatory cytokines as well as bacterial lipopolysaccharide. This inducibility appears strikingly restricted to endothelial cells derived from microvascular, but not large vessel sources, through the expression on the cell surface of CD44. Changes in mRNA levels for the described HA synthetic and degradative enzymes were not found initially, suggesting that retain HA extracelullar oligosaccharides generated during inflammation. However, it has been also shown than in some stress conditions endothelial cells increases endothelial hyaluronan synthase 2 and hyaluronan synthesis (Maroski J et al. 2011 Exp Physiol 96: 977-986). Therefore, the augment of anti-HA disaccharide antibodies at AHXR results from the presence of immunogenic HA on xenogeneic endothelial cells. This HA could be due to the production of the carbohydrate by xenogeneic endothelial cells or the binding of extracellular HA by these cells, which in this case would have a recipient origin. However, the changes observed with anti-HA disaccharide antibodies after PRBC exposure suggest that HA antigens responsible for this reactivity are generated from endogenous HA, since there is not any evidence of HA expression on RBC in contrast to what happens with endothelial cells.

Preformed Antibodies in Human Serum Against HA Disaccharide, HA Tetrasaccharide and HA Decasaccharide HA is constructed from disaccharide repeating units. Disaccharide repeating units can be 10,000 or more in hyaluronic acid in a living body. HA changes biological activities depending on its molecular weight. Biological features of high molecular hyaluronic acid is water-retention, maintenance of cell and differentiation control. Low molecular HA and HA oligosaccharides are known to have various activities which high molecular HA does not have. They induce cytokines and chemokines that are implicated in inflammation and degradation of extracellular matrix. In addition, there are many reports showing that low molecular weight HA is angiogenic, while, high molecular weight HA suppresses angiogenesis and production of cytokines.

Humans also have preformed antibodies against HA disaccharide (von Gunten S et al. 2009 J Allergy Clin Immunol 123: 1268-1276; Huflejt M E et al. 2009 Mol Immunol 46: 3037-3049). Thus, we used human serums randomly selected to investigate by specific ELISAS, the presence of preformed antibodies against HA disaccharide, tetrasaccharide and decasacchride. Also, antibodies against HA oligosaccharides were investigated in rats immunized either with PRBC and hamster blood following two protocols to generate mainly IgM or IgG antibodies.

Figure 5:
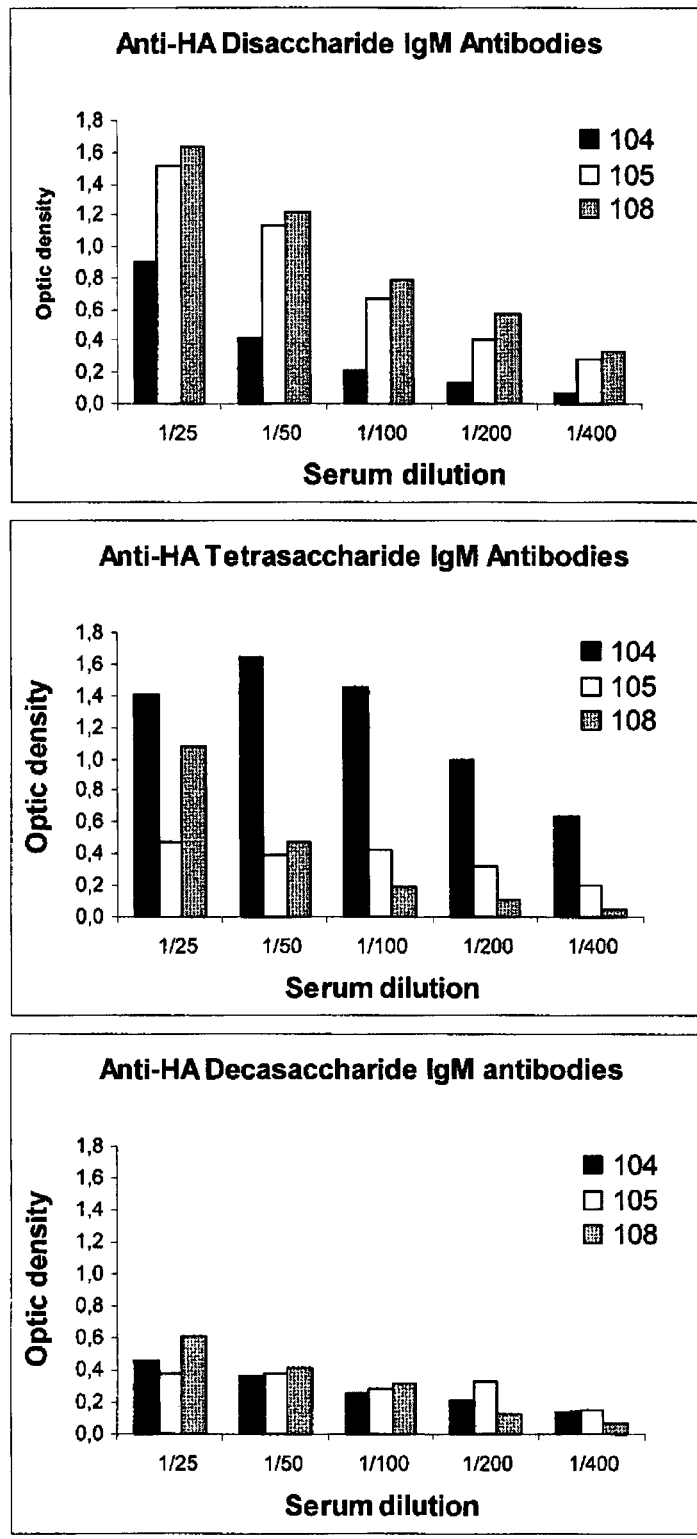
FIG. 5 shows the levels of preformed IgM and IgG anti-hyaluronic acid (anti-HA) disaccharide, tetrasaccharide and decasaccharide antibodies, in three randomly selected human serum samples.
Figure 5:
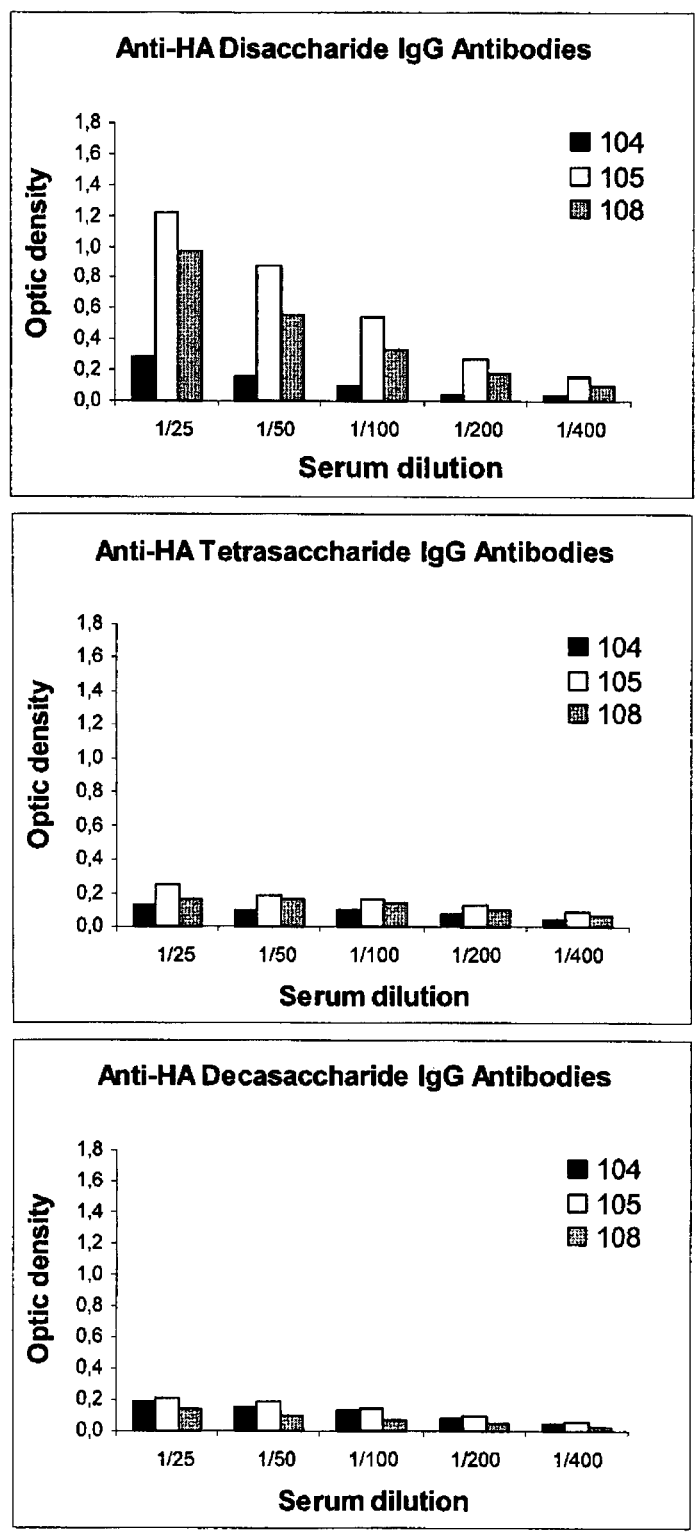
Figure 6:
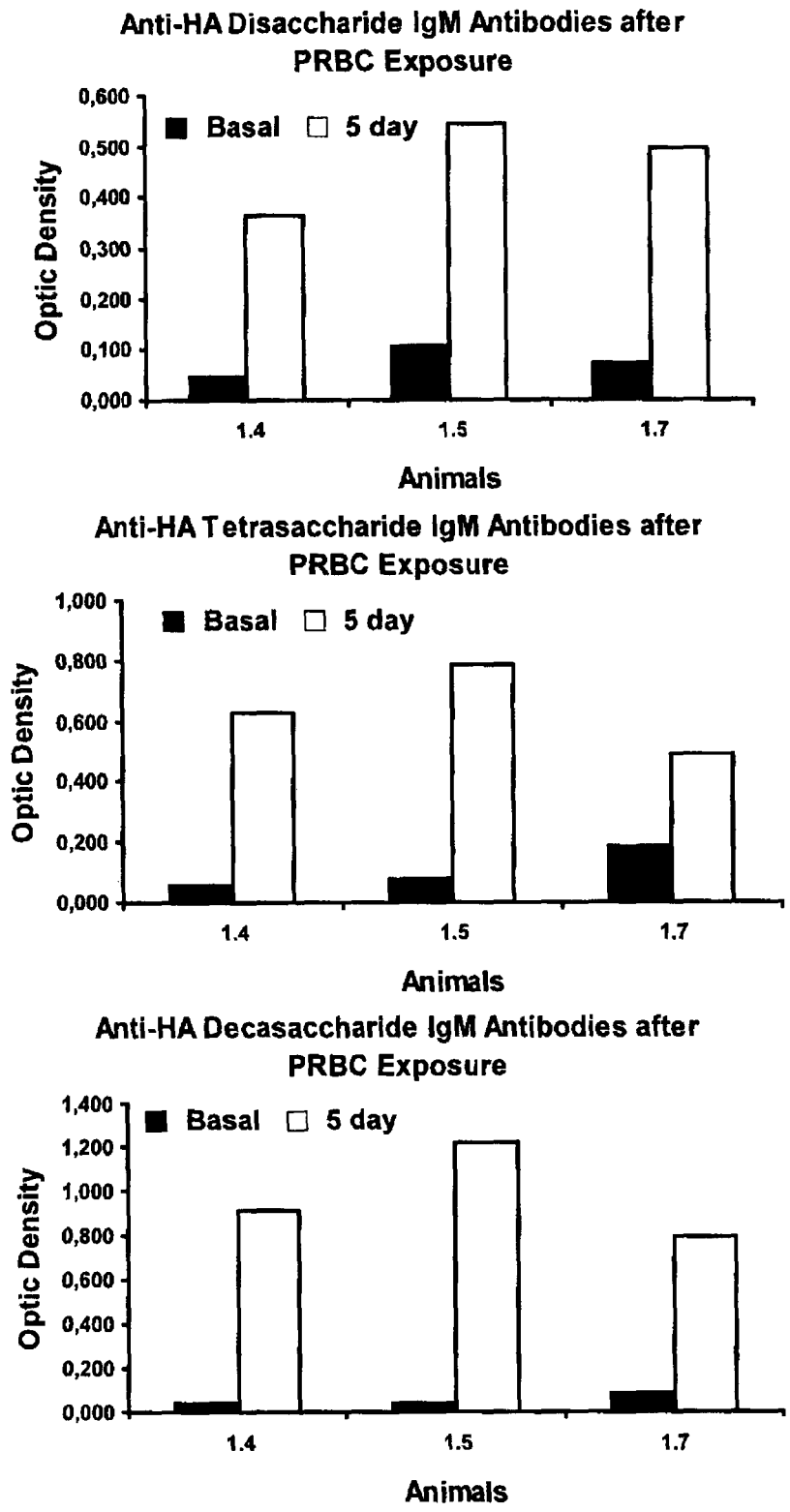
FIG. 6 shows the level of IgM anti-HA disaccharide, tetrasaccharide and decasaccharide antibodies, in rats before and after exposure to PRBC and hamster blood. The immunization protocol was as follows: 3 injections of 1 cc (days 0, 2, and 4) and blood drawn on the day 5 for analysis of antibodies
Figure 6:
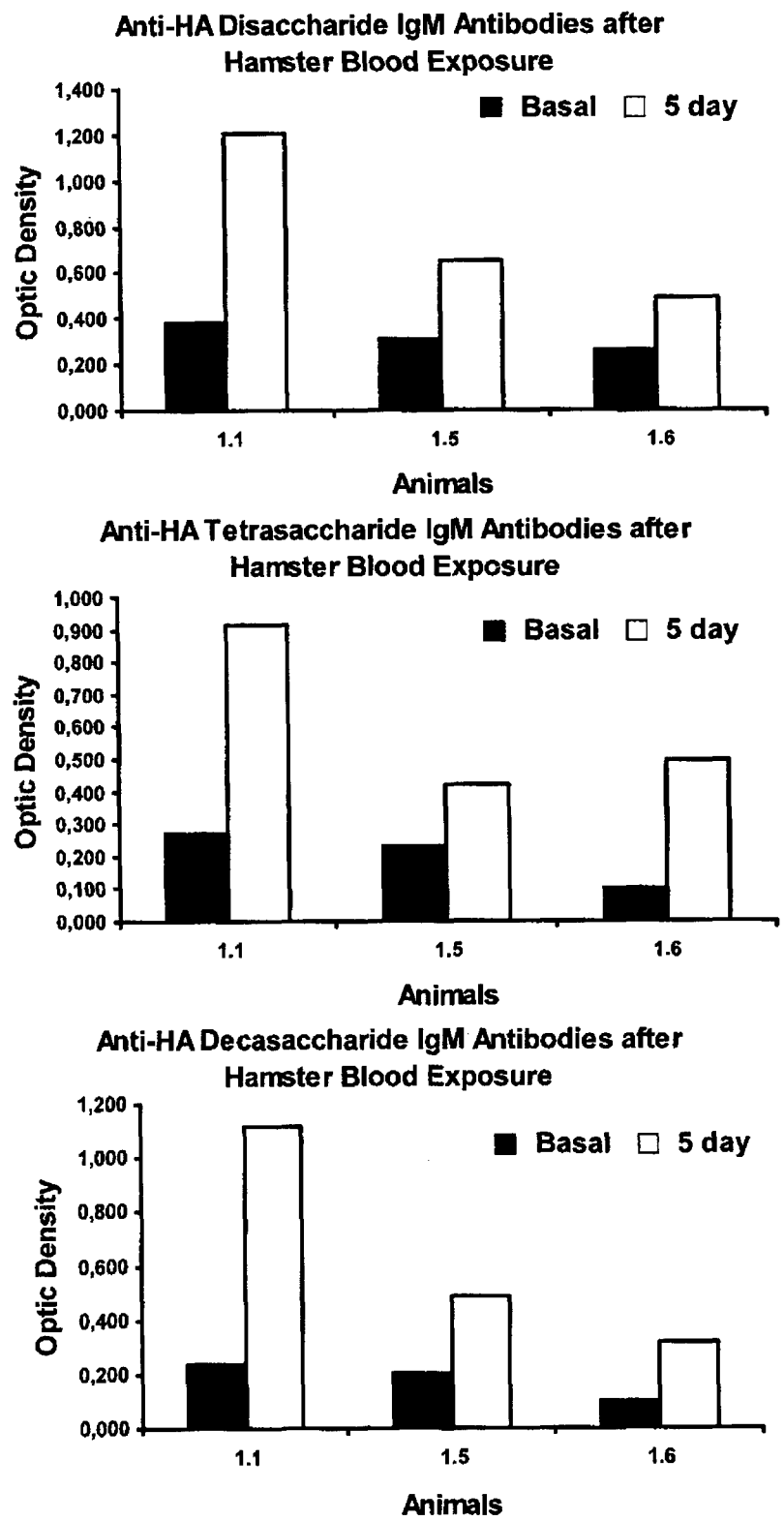
Figure 7:
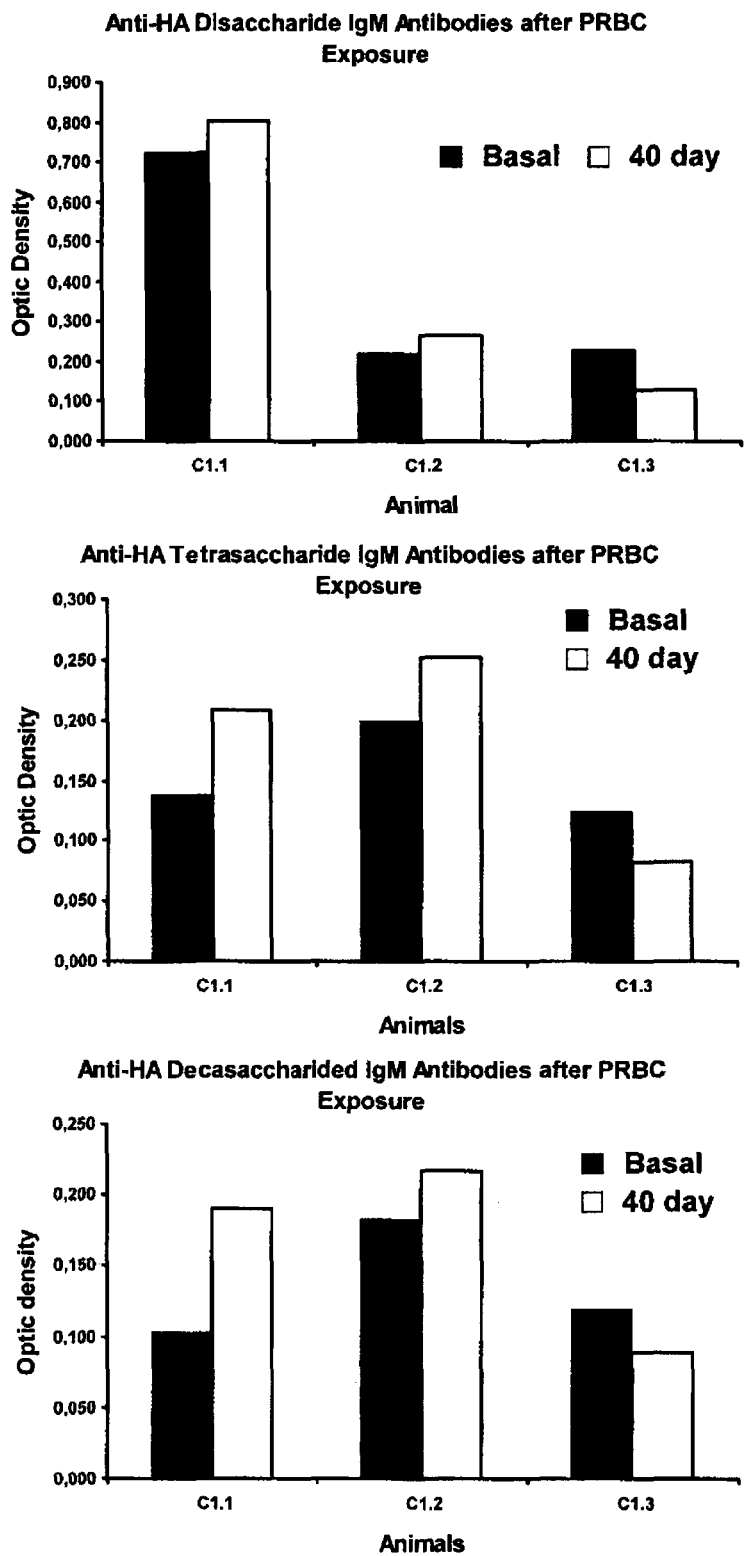
FIG. 7 shows the levels of IgM and IgG anti-HA disaccharide, tetrasaccharide and decasaccharide antibodies, in rats before and after exposure to PRBC. The immunization protocol was as follows: 3 injections of 1 cc. (days 0, 14 and 28) and blood drawn on day 40 for analysis of antibodies.
Figure 7:
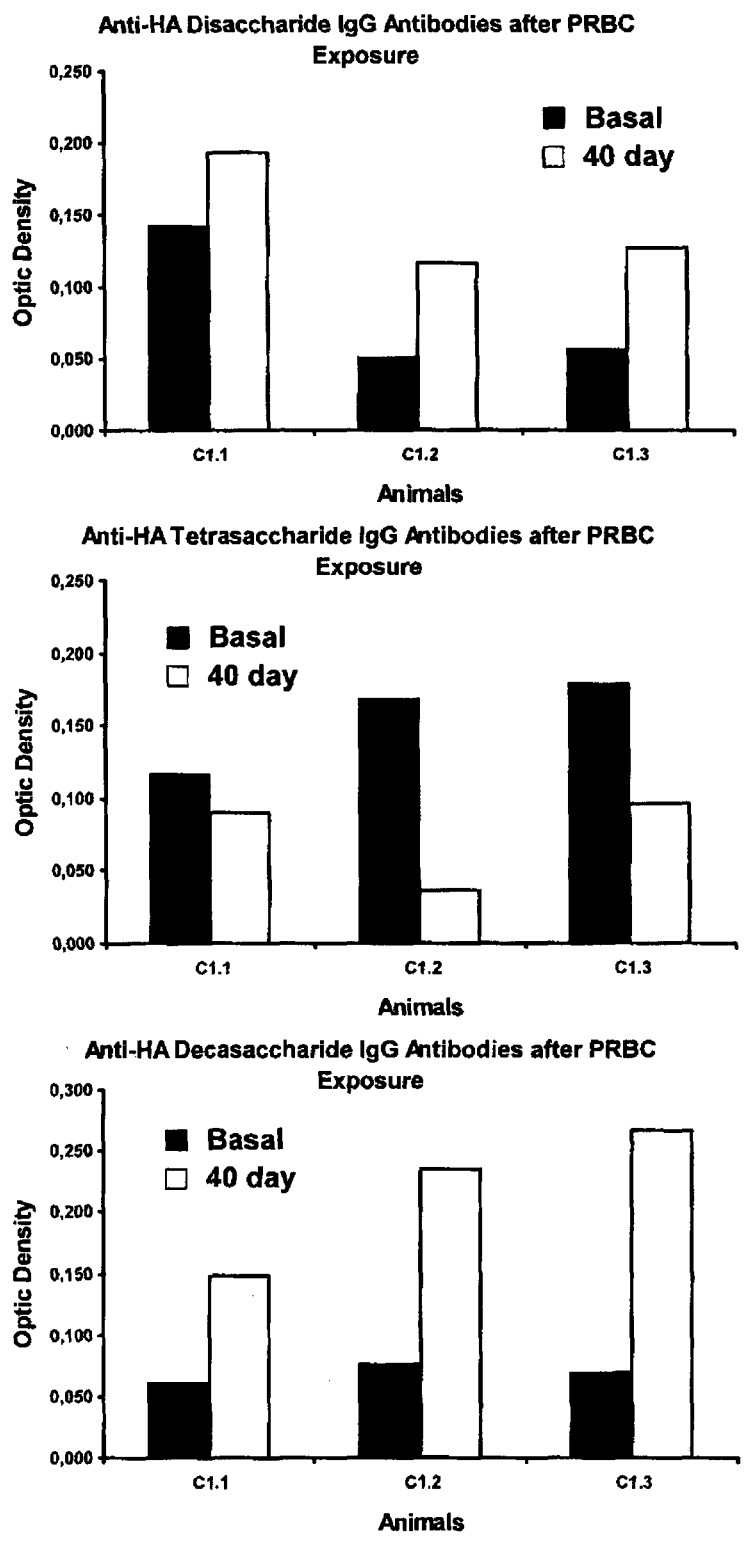
Figure 8:
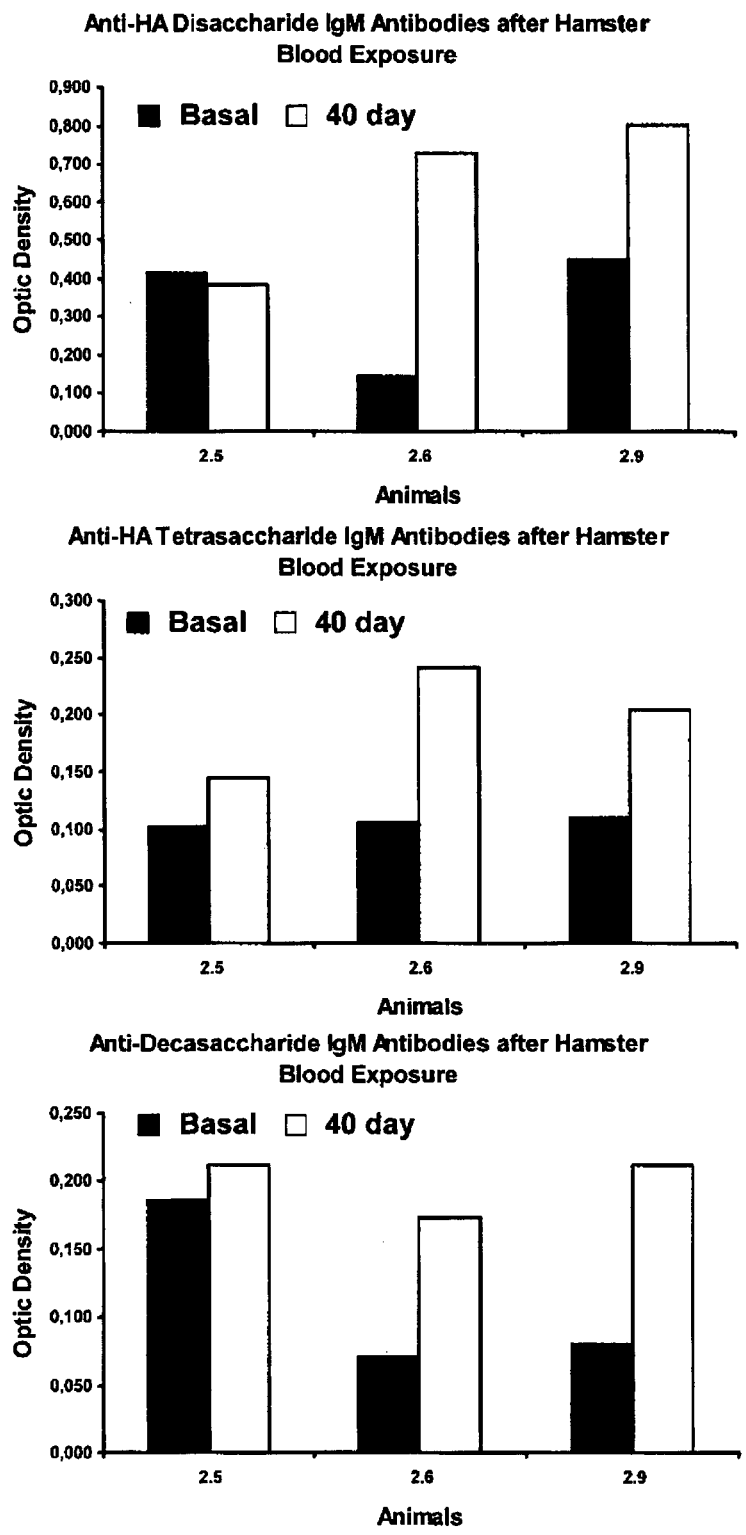
FIG. 8 shows the levels of IgM and IgG anti-HA disaccharide, tetrasaccharide and decasaccharide antibodies, in rats before and after exposure to hamster blood. The immunization protocol was as follows: 3 injections of 1 cc. (days 0, 14 and 28) and blood drawn on day 40 for analysis of antibodies.
Figure 8:
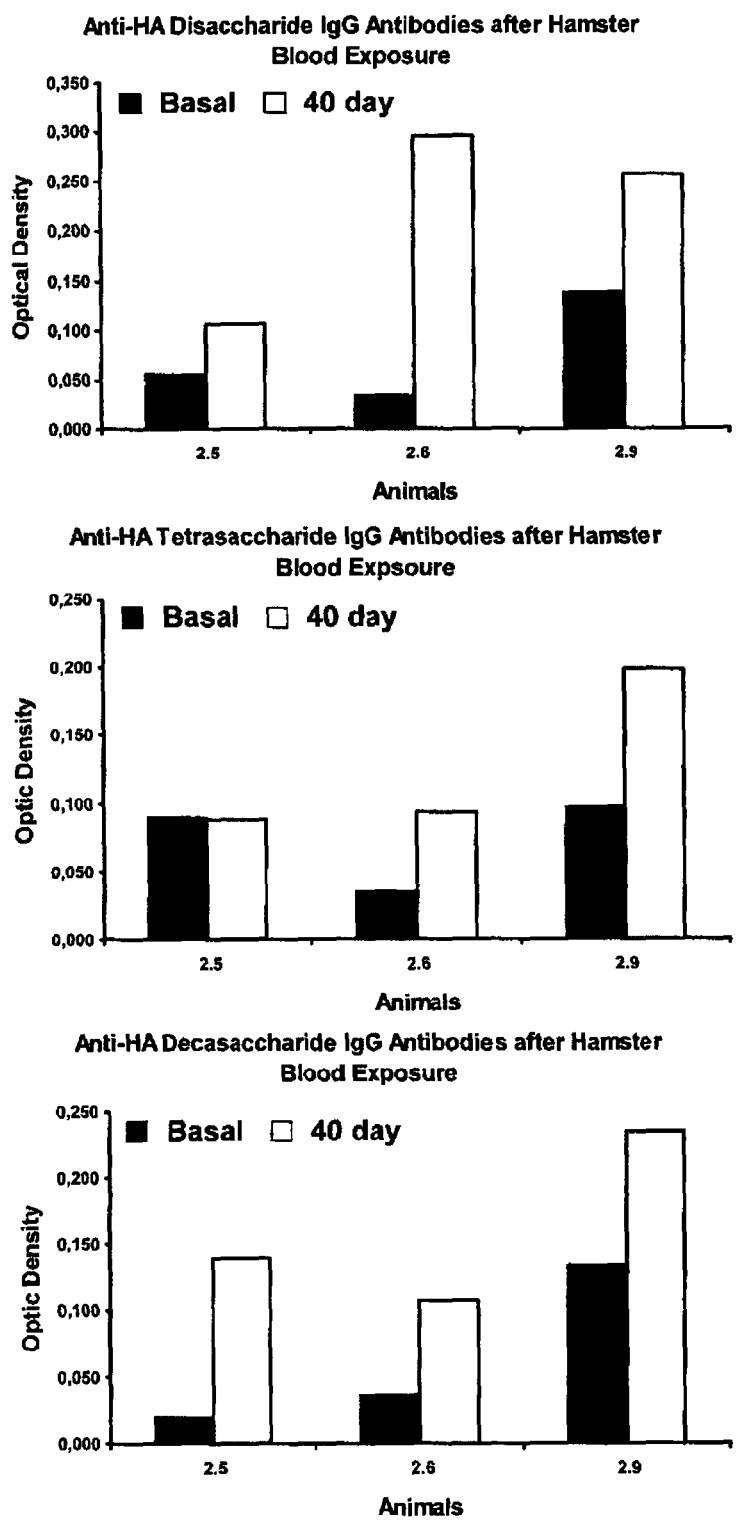

Humans have preformed IgM antibodies against HA disaccharide and tetrasaccharide, with a much lower titer against decasaccharide, whilst preformed IgG antibodies are only against HA disaccharide (FIG. 5). Rats have a lower level of preformed antibodies against HA disaccharide, tetrasaccharide and decasaccharide compared to humans, which in many cases were undetectable (FIG. 6). However, exposure to three injections of either PRBC or hamster blood every other day generates a significant production of IgM antibodies targeting HA disaccharide, tetrasaccharide and decasaccharide (FIG. 6). No IgG antibodies were detected against any of these HA oligosaccharides with this protocol of immunization. In contrast, exposure to three injections of PRBC every other week (FIG. 7) or hamster blood (FIG. 8), showed a variable production of anti-HA IgM antibodies, observed with hamster blood but not with PRBC, and a significant production of anti-HA disaccharide, tetrasaccharide and decasaccharide IgG antibodies with both protocols of immunization.

Figure 9:
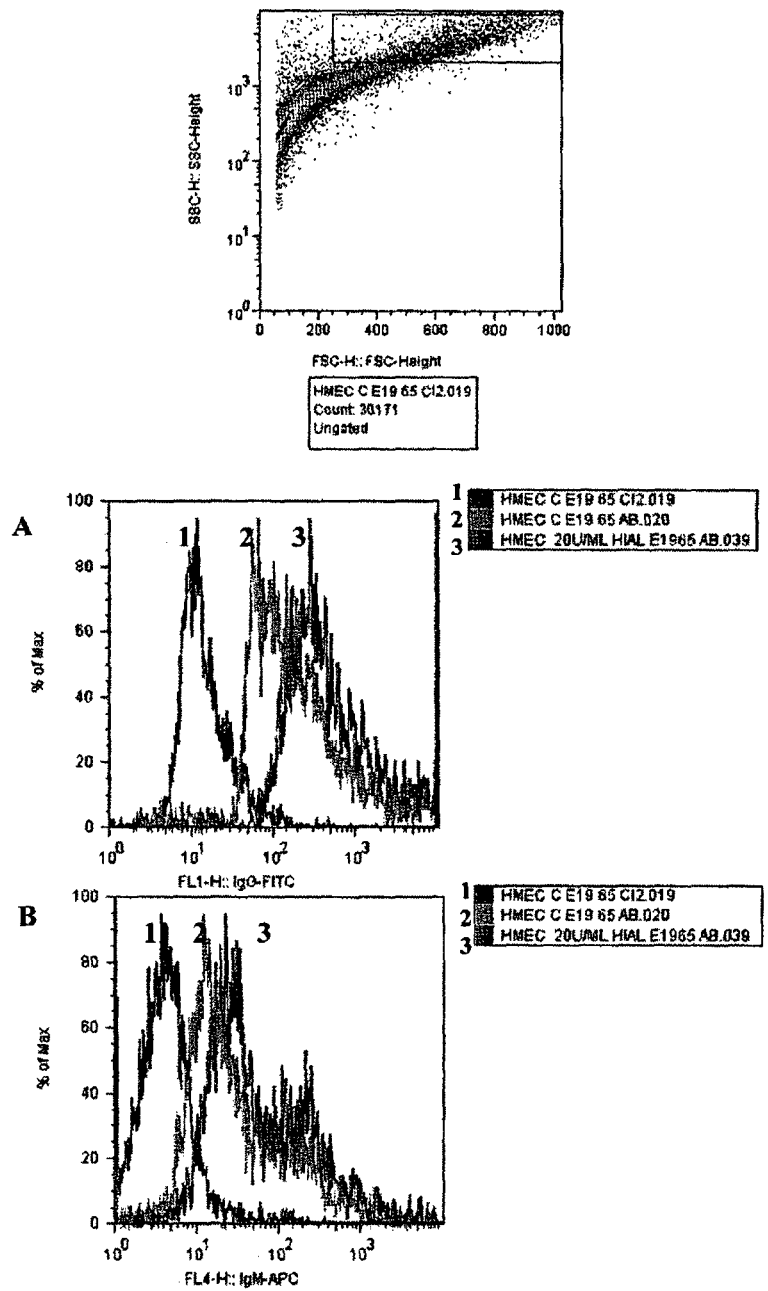
FIG. 9 shows the binding of IgG (A) and IgM (B) antibodies from non-human primates to human endothelial cells (HMEC) pre-treated with hyaluronidase from *Streptomyces*. Hyaluronan binding protein (HABP) was used as control (C). Three graphs are shown per histogram: graph 1 corresponds to the antibody alone, without any serum; graph 2 corresponds to antibodies in the serum of the subject immunized with HMEC cells, wherein said cells are not treated with hyaluronidase; graph 3 corresponds to antibodies in the serum of the subject immunized with HMEC cells, wherein said cells are pre-treated with hyaluronidase.
Figure 9:
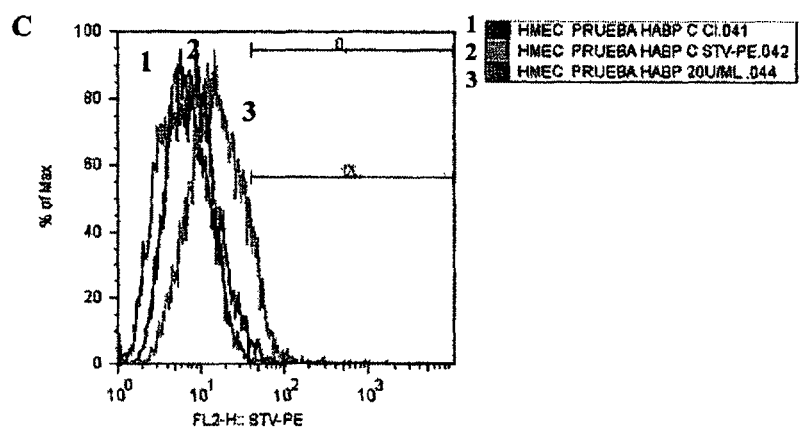

Pre-Treatment of Human Endothelial Cells with Hyaluronidase is Associated with an Augment of Serum Antibody Binding from Primates Immunized with Pig Blood The authors have previously shown that immunization of non-human primates with pig blood is associated with the generation of xenoantibodies cross-reactive to human endothelial cells. To investigate whether HA antigens were involved in this reactivity, human endothelial cells (HMEC) were pre-treated with 20 Um' of hyaluronidase from *Streptomyces*, which is specific for HA, for one hour. This hyaluronidase cleaves HA in fragments of 4 and 6 saccharides (tetra- and hexasaccharides). The flow cytometric results showed and augment of non-human primate IgG antibody binding to HMEC with hyaluronidase pre-treatment (FIG. 9A), which was not observed for IgM antibodies (FIG. 9B). This suggests that generation of tetra- and hexasaccharides of HA augments the immunogenicity of HMEC to serum from non-human primates immunized with porcine blood. To show the effect of hyaluronidase pre-treatment in HA on HMEC cells, a hyaluronan-binding-protein (HABP), which binds to large molecular weight HA, was used as control (FIG. 9C). In this case, pre-treatment of HMEC cells with hyaluronidase was associated with a reduction of HA expression, compared to the baseline, because the tetra- and hexasaccharide fragments are not bound by HABP.

Evaluation of these results along with those obtained in biopsies from pig organs transplanted in non-human primates, which showed a significant reduction of IgG antibodies with hyaluronidase pre-treatment, suggest that the most immunogenic HA oligosaccharides have at least 6 carbohydrates (hexasaccharide). The reason is that in the latter case hyaluronidase pre-treatment was performed when antibodies were already bound to HA, in contrast to HMEC studies in which the pre-treatment was performed before exposure to immunized non-human primate sera. The hyaluronidase generates in both cases fragments of 4 and 6 saccharides. Whilst the hexasaccharide can be cleaved in fragments of 4 and 2 by the same the hyalorunidase, the tetrasaccharide cannot be cut in fragments of 2. Therefore, the augment of antibody IgG binding observed in HMEC and the reduction in porcine tissue samples at the time of xenograft rejection, can only be explained with the generation of immunogenic hexasaccharides of HA.

Analysis of Anti-HA Disaccharide Antibodies in Patients with Systemic Lupus Erythematosus (SLE)

The level of antibodies against HA disaccharide were evaluated in a cohort of patients with SLE. The reason is that a recent study in SLE patients using an antigen microarray containing 694 antigens, identified anti-HA antibodies as one of four that were increased with the disease. The other three were antibodies against double-stranded DNA (dsDNA), single-stranded DNA (ssDNA) and Epstein-Barr virus (EBV).

This study also showed that SLE was associated with decreased IgM natural autoantibodies. The inventors analyzed the level of anti-HA disaccharide antibodies by specific ELISA in patients with SLE and anti-DNA antibodies (Group A; n=17), SLE without anti-DNA antibodies (Group B; n=10) and controls from blood bank (Group C; n=13). The values for IgM anti-HA disaccharide antibodies were (mean±S.E.) 0.58±0.07 in Group A, 0.71±0.13 in Group B, and 0.74±0.11 in Group C, with p=0.1 in ANOVA comparing Group A with Groups B or C. For IgG, the values were 0.37±0.08 in Group A, 0.27±0.05 in Group B, 0.27±0.03 in Group C, with a p=0.3 in ANOVA comparing Group A with Groups B or C. These results point to reduced IgM and augmented IgG anti-HA disaccharide antibodies in patients with SLE, suggesting that the changes in anti-HA antibodies observed may be related to the immunogenicity of particular HA oligosaccharides, not the whole HA molecule.

The invention claimed is:

1. An immunoabsorbent composition comprising hyaluronic acid oligosaccharides covalently bound, directly or by a linking arm, to a biocompatible solid support, wherein a hyaluronic acid oligosaccharide is an oligosaccharide which comprises at least one disaccharide unit with the following formula:

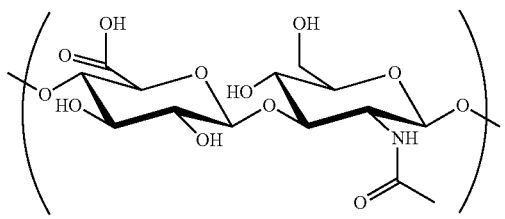

2. An immunoabsorbent composition according to claim 1 wherein the hyaluronic acid oligosaccharides are selected from the group consisting of hyaluronic acid disaccharides, hyaluronic acid tetrasaccharides, hyaluronic acid hexasaccharides, and/or hyaluronic acid decasaccharides.

3. A method of attenuating antibody-mediated transplant rejection in a subject recipient of a transplant comprising exposing an antibody-containing body fluid from the subject recipient to an immunoabsorbent composition according to claim 1.

4. A method of attenuating antibody-mediated transplant rejection in a subject recipient of a transplant, said method comprising:
(i) withdrawing antibody-containing body fluid from the recipient; and
(ii) removing antibodies to hyaluronic acid from the body fluid by extracorporeal perfusion of the body fluid over an immunoabsorbent composition according to claim 1 to yield a perfused body fluid for reintroduction into the recipient.

5. The method of attenuating antibody-mediated transplant rejection in a subject recipient of a transplant according to claim 4 wherein the antibodies to hyaluronic acid are antibodies targeting hyaluronic acid disaccharides, hyaluronic acid tetrasaccharides, hyaluronic acid hexasaccharides, and/or hyaluronic acid decasaccharides.

6. The method of attenuating antibody-mediated transplant rejection in a subject recipient of a transplant according to claim 4 wherein the body fluid is blood.

7. The immunoabsorbent composition according to claim 1, wherein the biocompatible solid support is a polymeric structure comprising a polymeric backbone wherein one or more of the monomer units forming the polymeric backbone are linked to said hyaluronic acid oligosaccharides.

8. The immunoabsorbent composition according to claim 7, wherein the polymeric backbone is selected from the group consisting of a polyamide, a polycarbonate, a polyiminocarbonate, a polyanhydride, a polyorthoester, a polyester, a polydioxanone, a polyhydroxycarboxylic acid, a polyaminoacid, a polyphosphazene, a polysaccharide, and or combinations thereof.

9. The immunoabsorbent composition according to claim 7, wherein the hyaluronic acid oligosaccharide is selected from the group consisting of a hyaluronic acid disaccharide, a hyaluronic acid tetrasaccharide, a hyaluronic acid hexasaccharide, a hyaluronic acid decasaccharide and a mixture thereof.

10. A method for attenuating antibody-mediated transplant rejection in a subject recipient of a transplant comprising exposing an antibody-containing body fluid from the subject recipient to an immunoabsorbent composition according to claim 7.

11. The method of attenuating antibody-mediated transplant rejection in a subject recipient of a transplant according to claim 10 wherein said hyaluronic acid oligosaccharide is selected from the group consisting of a hyaluronic acid disaccharide, a hyaluronic acid tetrasaccharide, a hyaluronic acid hexasaccharide, a hyaluronic acid decasaccharide or a mixture of one or more of the above.

12. An immunoabsorbent composition according to claim 1, wherein the hyaluronic acid oligosaccharides are covalently bound, by the linking arm, to the biocompatible solid support.

13. An immunoabsorbent composition according to claim 12, wherein the linking arm is formed by reaction between a spacer which carries two reactive functional groups, and activated groups on the hyaluronic acid oligosaccharides and the biocompatible solid support;
said reactive functional groups being selected from the group consisting of OH, $NH_2$, SH, and combinations thereof; and
said activated groups being selected from the group consisting of aldehyde groups, acrylic esters, acrylamides, malonimide, succinimide, 2-vinylpyridine, iodoacetic esters, isothiocyanate, isocyanate, and mixtures thereof.

14. An immunoabsorbent composition according to claim 1, wherein:
the immunoabsorbent composition is adapted for use in a system for extracorporeal perfusion of a body fluid, and
the biocompatible solid support is adapted to allow the body fluid to flow therethrough.

15. An immunoabsorbent composition according to claim 1, wherein the composition is immunoabsorbent towards anti-hyaluronic acid antibodies.

* * * * *